(12) United States Patent
Escriou et al.

(10) Patent No.: US 9,572,776 B2
(45) Date of Patent: Feb. 21, 2017

(54) VECTORS INCLUDING AN ANIONIC MACROMOLECULE AND A CATIONIC LIPID FOR DELIVERING SMALL NUCLEIC ACIDS

(75) Inventors: Virginie Escriou, Villejuif (FR); Pascal Bigey, Paris (FR); Daniel Scherman, Paris (FR)

(73) Assignees: CENTRE NATIONAL DE LA RECHERCHE SCIENTIFIQUE (CNRS), Paris (FR); UNIVERSITE PARIS DESCARTES, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 13/145,008

(22) PCT Filed: Jan. 20, 2010

(86) PCT No.: PCT/EP2010/050635
§ 371 (c)(1),
(2), (4) Date: Dec. 28, 2011

(87) PCT Pub. No.: WO2010/084129
PCT Pub. Date: Jul. 29, 2010

(65) Prior Publication Data
US 2012/0093915 A1    Apr. 19, 2012

(30) Foreign Application Priority Data

Jan. 20, 2009  (FR) ..................................... 09 50336

(51) Int. Cl.
| | | |
|---|---|---|
| *A61K 31/7088* | (2006.01) | |
| *A61K 9/127* | (2006.01) | |
| *C12N 5/071* | (2010.01) | |
| *A61P 25/28* | (2006.01) | |
| *A61P 35/00* | (2006.01) | |
| *A61P 19/02* | (2006.01) | |
| *A61K 31/713* | (2006.01) | |
| *A61P 1/16* | (2006.01) | |
| *A61K 47/34* | (2006.01) | |
| *A61K 47/36* | (2006.01) | |
| *A61K 47/48* | (2006.01) | |
| *C12N 15/87* | (2006.01) | |
| *C12N 15/88* | (2006.01) | |

(52) U.S. Cl.
CPC ............ *A61K 9/1272* (2013.01); *A61K 47/34* (2013.01); *A61K 47/36* (2013.01); *A61K 47/48815* (2013.01); *C12N 15/87* (2013.01); *C12N 15/88* (2013.01)

(58) Field of Classification Search
USPC ........................................................ 424/450
See application file for complete search history.

(56) References Cited

U.S. PATENT DOCUMENTS

| | | | | |
|---|---|---|---|---|
| 5,264,618 | A | * | 11/1993 | Felgner et al. ............... 560/224 |
| 6,171,612 | B1 | | 1/2001 | Byk et al. |
| 7,173,116 | B2 | * | 2/2007 | Fewell et al. ................ 536/23.1 |
| 2003/0054007 | A1 | * | 3/2003 | Felgner et al. ............ 424/178.1 |
| 2004/0198687 | A1 | * | 10/2004 | Rozema et al. ................ 514/44 |
| 2010/0260817 | A1 | * | 10/2010 | Slobodkin et al. .......... 424/426 |

FOREIGN PATENT DOCUMENTS

| | | | |
|---|---|---|---|
| EP | 1046394 | * | 10/2000 |
| EP | 1 938 802 A1 | | 7/2008 |
| FR | 2 858 628 | | 2/2005 |
| WO | WO 9718185 A1 | | 5/1997 |
| WO | WO-03-095641 | * | 11/2003 |
| WO | WO 03/095641 A1 | | 11/2003 |

OTHER PUBLICATIONS

Sorenson DR, Gene silencing by systemic delivery of synthetic siRNAs in adult mice, Science Direct, JMolBiol, 2003, 327, 761-766.*
International Search Report issued in application No. PCT/EP2010/050635 on Mar. 22, 2010.
Khoury et al., "Efficient Delivery of Small Interfering Rna Targeting Pro-Inflammatory Cytokines in Experimental Arthritis," Arthritis and Rheumatism, vol. 54, No. 9, Suppl. S, p. S174, Sep. 1, 2006.
Khoury et al., "Efficient New Cationic Liposome Formulation for Systemic Delivery of Small Interfering RNA Silencing Tumor Necrosis Factor α in Experimental Arthritis," Arthritis and Rheumatisim, vol. 54, No. 6, pp. 1867-1877, Jun. 2006.
Van Ommen et al., "The therapeutic potential of antisense-mediated exon skipping," Current Opinion in Molecular Therapeutics, vol. 10, No. 2, pp. 140-149, 2008.
Byk et al., "Synthesis Activity and Structure—Activity Relationship Studies of Novel Cationic Lipids for DNA Transfer," J. Med. Chem., vol. 41, pp. 224-235, 1998.
Rhinn et al., "How to make siRNA lipoplexes efficient? Add a DNA cargo," Biochimica et Biophysica Acta, vol. 1790, pp. 219-230, 2009.
Kaur et al., "Therapeutic applications of aptamers," Expert Opin. Investig. Drugs, vol. 17, No. 1, pp. 43-60, 2008.
Patanaik et al., "PEI-alginate nanocomposites as efficient in vitro gene transfection agents," Journal of Controlled Release, vol. 114, pp. 398-409, 2006.
Wu et al., "Let me count the Ways: Mechanisms of Gene Regulation by miRNAs and siRNAs," Molecular Cell, vol. 29, pp. 1-7, Jan. 18, 2008.

(Continued)

*Primary Examiner* — Frederick Krass
*Assistant Examiner* — Celeste A Roney
(74) *Attorney, Agent, or Firm* — Foley & Lardner LLP

(57) ABSTRACT

The invention relates to a composition including (1) an anionic macromolecule except nucleic acids, (2) a cationic lip, and (3) a nucleic acid having a size lower than or equal to 200 nucleotides, such as an interference RNA, and to the use thereof in gene therapy.

12 Claims, 11 Drawing Sheets

(56) References Cited

OTHER PUBLICATIONS

Schlegel et al., "Anionic polymers for decreased toxicity and enhanced in vivo delivery of siRNA complexed with cationic liposomes," Journal of Controlled Release, vol. 152, pp. 393-401, 2011.
Thierry et al.,"Characterization of liposome-mediated gene delivery: Expression, stability and pharamacokinetics of plasmid DNA," Gene Therapy, vol. 4, pp. 226-237, 1997.
Yang et al., "Overcoming the inhibitory effect of serum on lipofection by increasing the charge ratio of cationic liposome to DNA," Gene Therapy, vol. 4, No. 9, pp. 950-960, Sep. 1997.
Bragonzi et al., "Biodistribution and transgene expression with nonviral cationic vector/DNA complexes in the lungs," Gene Therapy, vol. 7, pp. 1753-1760, 2000.
Peters et al., "Optimization of cationic liposome-mediated gene transfer to human bronchial epithelial cells expressing wild-type or abnormal cystic fibrosis transmembrane conductance regulator (CFTR).," Exp Lung Res., vol. 25, No. 3, pp. 183-197, Apr.-May, 1999.
Watts et al., "Chemically modified siRNA: tools and applications," Drug Discovery Today, vol. 13, Nos. 19/20, pp. 842-855, Oct. 2008.
Kisoon et al., "A novel cationic cholesterol derivative, its formulation into liposomes, and the efficient transfection of the transformed human cell lines HepG2 and HeLa," vol. 9, No. 3, pp. 161-167, Jul.-Sep. 2002.
Spagnou et al., "Lipidic Carriers of siRNA: Differences in the Formulation, Cellular Uptake, and Delivery with Plasmid DNA," Biochemistry, vol. 43, pp. 13348-13356, 2004.
Wolff et al., "Expression of naked plasmids by cultured myotubes and entry of plasmids into T tubules and caveolae of mammalian skeletal muscle," J Cell Sci, vol. 103, pp. 1249-1259,1992.
Grayson et al., "Biophysical and Structural Characterization of Polyethylenimine-Mediated siRNA Delivery in Vitro," Pharm Res, vol. 23, No. 8, pp. 1868-1876, Aug. 2006.

\* cited by examiner

VECTORS INCLUDING AN ANIONIC MACROMOLECULE AND A CATIONIC LIPID FOR DELIVERING SMALL NUCLEIC ACIDS

The present invention relates to novel vectors for the intracellular administration of nucleic acids of small size, such as nucleic acids able to modulate a protein function, and to the use of same in gene therapy.

Numerous diseases are associated with faulty expression and/or abnormal expression, i.e., deficient or excessive expression, of one or more nucleic acids. The principal goal of gene therapy is to correct these types of genetic anomalies by means of the cellular expression in vivo or in vitro of cloned genes.

Numerous nucleic acids of small size, such as interfering RNA (miRNA, siRNA, etc.) are able to control the expression of a protein in a specific manner by acting on the mRNA of the protein in question. They recruit protein complexes that destroy mRNA, which leads to the loss of the expression of this protein as well as its function. The site of action of these small nucleic acids is the cell cytoplasm. However, it is difficult for a nucleic acid to cross the cell membrane without it being associated with a vector. In the absence of a vector, weak penetration can be obtained on the condition of adding the nucleic acid at very high concentrations which, in addition to being expensive in terms of product, leads to nonspecific extinction of all proteins of the cell as well as to toxicity.

The vectors the most commonly used and the most effective for enabling nucleic acids to penetrate into the cytoplasm of a cell are cationic chemical molecules, specifically lipids or polymers, which combine to share their charge with the nucleic acid and thus enable it to enter the cell. These molecules are used quite commonly to enable nucleic acids (DNA or RNA, small or large) to penetrate into cells in culture or into cells of an organism. Highly effective in cells in culture, they are less so in an organism because of phenomena of trapping by proteins and cells contained in blood. In addition, it should be noted that small nucleic acid molecules are able to interact with a cationic lipid but the complexes formed do not necessarily have the same properties as complexes formed with large DNA.

It has been proposed to associate a nucleic acid molecule with PEI-alginate (PATNAIK et al., 2006). Alginic acid is used to mask the charges of PEI (polyethylenimine, a cationic polymer), independently of the nucleic acid molecule (DNA-RNA) which is associated thereafter. The finality of the addition of alginic acid is thus different than that of the present invention, since in PATNAIK et al. (2006) the issue is not one of assisting the formation of complexes between the cationic lipid and the small nucleic acid molecule by adding a macromolecule.

It has also been proposed to use a large double-stranded DNA (called DNA cargo), whose sole function is to assist the association of siRNA with the vector (KHOURY et al., 2006). This DNA cargo is a supercoiled circular double-stranded plasmid DNA.

However, dsDNA cargo carries nucleotide sequences that can be transcribed by the cellular machinery of the cell receiving the vector, which is not compatible with clinical applications of the preparation.

Moreover, such vectors must be nontoxic and biodegradable while being stable in the presence of serum, notably for clinical applications.

The Inventors solved this problem by developing a composition comprising a certain type of anionic macromolecule and a cationic lipid as a small nucleic acid vector. Such a composition makes it possible to improve the vectorization of small nucleic acids while being nontoxic, biodegradable and stable in the presence of serum.

A major difference between dsDNA cargo and anionic polymers such as alginic acid or polyglutamic acid is that dsDNA cargo has a very particular topology: it is a supercoiled circular double-stranded plasmid DNA commonly used in combination with cationic lipids. On the other hand, alginic acid is generally used for its ability to form insoluble gels, and polyglutamic acid is used in grafting on hydrophobic compounds to increase their solubility in water. These polymers do not have a particular topology like plasmid DNA.

However, it is well known to the person skilled in the art that nucleic acids, such as plasmid DNA, are able to combine with cationic lipids, and that this is not at all the case for any other anionic polymer. In addition, nucleic acids are often relatively rigid double-stranded macromolecules, which is not inevitably the case with anionic polymers in general. Thus, it was not obvious that a non-nucleotide anionic polymer is able to form ternary combinations with a cationic lipid and a nucleic acid, thus resulting in an increase in the biological effect of the small nucleic acids incorporated in such ternary complexes. Indeed, it would have been easy to imagine that it only forms a mixture of binary complexes, composed of lipids and nucleic acid on one hand and lipids and polymer on the other.

Thus, the present invention relates to a composition comprising:

(1) an anionic macromolecule except for nucleic acids,
(2) a cationic lipid, and
(3) a nucleic acid of size less than or equal to 200 nucleotides.

In the present invention, "anionic macromolecule" refers to a molecule of high molecular weight having an overall negative charge, except for nucleic acids.

In the context of the present invention, "nucleic acid" refers to a polymer whose basic unit is the nucleotide, wherein the various nucleotides are bound to each other by phosphodiester bonds.

A macromolecule generally results from the assembly, notably by covalent bonds, of a large number of similar or different chemical groups named repeating units.

The anionic macromolecule of the present invention can be a polymer or can be formed by self-association, via hydrogen bonds, of complementary monomers.

Preferably, the anionic macromolecule of the present invention is selected from anionic polysaccharides, anionic polypeptides, synthetic polyelectrolytes such as sodium polystyrene sulfonate and carboxymethyl cellulose (CMC), polyphosphates and polysaccharides such as dextran.

In a particularly preferred manner, the anionic macromolecule of the present invention is selected from polyphosphates, anionic polysaccharides and anionic polypeptides, even more preferentially from anionic polysaccharides and anionic polypeptides.

As defined in the present invention, a "polysaccharide" is formed by sequences of saccharides connected by glycosidic bonds, and an "anionic polysaccharide" is a polysaccharide with an overall negative charge.

Among the anionic polysaccharides, one can cite carrageenans (sulfated polysaccharides of red algae), fucans (sulfated polysaccharides of brown algae), carboxymethyl dextran benzylamide sulfonates or CMDBS (synthetic polysaccharides prepared from dextran by statistical substitution of hydroxyl functions by carboxymethyl chemical functions, benzylamides, sulfonates and sulfates), and heparan sulfates (complex polysaccharides, belonging to the family of glycosaminoglycans).

Advantageously, the anionic polysaccharide is alginic acid or a salt thereof, such as the sodium salt (SIGMA ALDRICH). Alginic acid (CAS: 9005-32-7) is a colloidal polysaccharide extracted from various varieties of brown algae, in particular *Laminaria*. Its constitutive monomers are alpha-L-glucuronic acid and beta-D-mannuronic acid bound per pair by 1→4 bonds. Alginic acid is made up on average of 200 basic units of uronic acid. Its molecular weight is generally between 10,000 Daltons and 600,000 Daltons.

As defined in the present invention, a "polypeptide" is a linear polymer composed of amino acids bound by covalent bonds, and an "anionic polypeptide" is a polypeptide with an overall negative charge.

The anionic polypeptide can be any natural or synthetic anionic polypeptide. It can be a mixed polyglutamic-polyaspartic polypeptide, or a polypeptide with an overall negative charge from natural amino acids (aspartic acid, glutamic acid) or non-natural amino acids.

Advantageously, the anionic polypeptide is polyglutamic acid or a salt of same, such as the sodium salt (SIGMA ALDRICH), or polyaspartic acid or a salt thereof, or dextran sulfate or a salt thereof, such as the sodium salt (such as that available from SIGMA ALDRICH) or carboxymethyl cellulose or a salt thereof, such as the sodium salt (such as that available from SIGMA ALDRICH), or polyacrylic acid or a salt thereof, such as the sodium salt (such as that available from Fluka).

Polyglutamic acid is a polymer that is soluble in water, biodegradable, edible and nontoxic.

Preferably, the anionic macromolecule has an average molecular weight between 1,000 Da and 1,000,000 Da, preferentially between 1,000 Da and 100,000 Da, even more preferentially between 4,300 Da and 56,000 Da. The average molecular weight will depend on the type of polymer and its preparation pathway (chemical synthesis or purification from biological material).

In the present invention, "cationic lipid" refers to a lipid having an overall positive charge. A cationic lipid is composed of a cationic polar head and a hydrophobic entity, namely lipid chains or cholesterol. Preferably, the cationic lipid is selected from:

Lipopolyamines, such as 2-{3-[bis-(3-amino-propyl)-amino]-propylamino}-N-ditetradecyl carbamoyl methyl-acetamide (compound RPR209120), 2-{3-[3-(3-amino-propylamino)-propylamino]-propylamino}-N,N-dioctadecyl-acetamide (RPR120535) (Byk et al., J. Med. Chem., 41, 224-235, 1998) or 2,3-dioleoyloxy-N-[2-(sperminecarboxamido)ethyl]-N,N-dimethyl-1-propane-aminium-trifluoracetate (DOSPA), dioctadecylamine-glycine-spermine (DOGS), dipalmitylphosphatidylethanolamine 5-carboxyspermylamide (DPPES), as well as all the lipopolyamines described from page 2, line 27 to page 4, line 19 in International application WO97/18185 as published, advantageously the lipopolyamines of the formula selected from formulas III to XII from page 5, line 1 to page 7, line 9 of application WO97/18185 as published, and in an even more advantageous way from page 8, line 29 to page 14, line 15 of application WO97/18185 as published.

Quaternary ammoniums such as 1,2-dimyristoyloxypropyl-3-dimethyl-hydroxy ethyl ammonium bromide (DMRIE), N-(2,3-dioleyloxypropyl]-N,N,N-trimethyl-ammonium chloride (DOTMA), 1,2-dioleoyloxypropyl-N,N,N-trimethylammonium chloride (DOTAP), dimethyldioctadecylammonium bromide (DDAB), or 1,2-dioleyloxypropyl-3-dimethylhydroxyethylammonium bromide (DORIE), and Lipids composed of guanidine (BGTC) or imidazole (DOTIM) cationic heads.

Preferably, the cationic lipid is formulated either in the form of micelles, or in the form of liposomes by association with a neutral lipid such as dioleyl phosphatidyl ethanolamine (DOPE, purchased from AVANTI POLAR LIPIDS), cholesterol, or (F8E11)(C16)OPE (also called N'-(rac-1-[11-(F-octyl)undec-10-enyl]-2-(hexadecyl)glycero-3-phosphoethanoyl)-sperminecarboxamide), preferably dioleyl phosphatidyl ethanolamine.

The cationic lipid can also be formulated by carrying out ethanol injections or by preparing it with a detergent.

Said composition according to the invention can also include polyethylene glycol (PEG), notably when said composition is used for applications in vivo, such as enabling nucleic acids to penetrate into cells of an organism.

The presence of PEG in the compositions according to the invention permits notably to increase the colloidal stability of the lipoplexes of the invention.

The composition of the invention can comprise between 0.1% and 10%, in particular between 1% and 5%, by weight of PEG relative to the total weight of lipids in the composition according to.

Preferably, the micelles are prepared by the addition of water or of buffer to the cationic lipid, then, after vigorous agitation the mixture is subjected to several cycles of freezing/heating at 55° C. until a clear suspension of micelles is obtained.

As a liposomal preparation one can cite LipofectAmine (Gibco BRL), which is prepared from DOSPA (lipopolyamine) and from DOPE (neutral lipid).

Advantageously, the cationic lipid is present in a quantity comprised between 1 nmol and 20 nmol per µg of the mixture of the nucleic acid and the anionic macromolecule, even more advantageously between 3 nmol and 8 nmol per µg of the mixture of the nucleic acid and the anionic macromolecule, and in a more preferred manner between 4 nmoles and 6 nmoles per µg of the mixture of the nucleic acid and the anionic macromolecule.

In the context of the present invention, "nucleic acid of size less than or equal to 200 nucleotides" or "small nucleic acid" refers to a deoxyribonucleic acid (DNA), a single- or double-stranded ribonucleic acid (RNA), or hybrid DNA/RNA sequences of size less than or equal to 200 nucleotides. They can be sequences of natural or artificial origin. They can also be obtained by a chemical modification at their sugars parts, their nucleobase parts or their internucleotide backbone. Among the advantageous modifications in the sugar parts notably include modifications intervening in position 2' of the ribose, such as 2'-deoxy, 2'-fluoro, 2'-amino, 2'-thio, or 2'-O-alkyl modifications, in particular 2'-O-methyl, in place of the normal 2'-OH group on the ribonucleotides, or the presence of a methylene bridge between positions 2' and 4' of the ribose (LNA). Concerning nucleobases, it is possible to use modified bases notably such as 5-bromo-uridine, 5-iodo-uridine, $N^3$-methyl-uridine, 2,6-diaminopurine (DAP), 5-methyl-2'-deoxyCytidine, 5-(1-propynyl)-2'-deoxy-Uridine (pdU), 5-(1-propynyl)-2'-deoxyCytidine (pdC), or bases conjugated with cholesterol. Lastly, advantageous modifications of the internucleotide backbone comprise the replacement of phosphodiester groups of this backbone by phosphorothioate, methylphosphonate or phosphorodiamidate groups, or the use of a backbone composed of units of N-(2-aminoethyl)-glycine bound by peptide bonds (PNA, Peptide Nucleic Acid). The various modifications (base, sugar, backbone) can of course be combined to give modified nucleic acids, namely morpholinos (bases fixed on a morpholine ring and bound by phosphorodiamidate groups) or PNAs (bases fixed on units of N-(2-aminoethyl)-glycine bound by peptide bonds).

Preferably, the nucleic acid of size less than or equal to 200 nucleotides is a nucleic acid able to modulate a protein function.

In the present invention, "nucleic acid able to modulate a protein function" refers to a nucleic acid which (1) either increases and/or restores, at least partially, (2) or inhibits and/or delays and/or blocks a protein function.

Such nucleic acids are well known to those persons skilled in the art. They are, for example, nucleic acids acting on the expression of a gene, such as antisense oligonucleotides or interfering RNA (miRNA, siRNA, etc.). They can also be oligonucleotides for exon skipping or the modification of alternative splicing. They can also be aptamers.

"Antisense oligonucleotide" refers to a nucleotide sequence complementary to another nucleotide sequence, such as a sequence of mRNA, which binds with the latter and prevents its translation into the corresponding protein, or penetrates in the nucleus, binds with a strand of DNA, and forms a DNA triple helix which cannot be transcribed into RNA.

"Interfering RNA" refers to a single- or double-stranded ribonucleic acid which interferes with a specific messenger RNA leading to its degradation and a reduction in its translation into protein. These are notably small interfering RNA (siRNA) and microRNA (miRNA) (Wu et al., 2008).

"Oligonucleotide for exon skipping" refers to a specific nucleotide sequence of a pre-messenger RNA and able to interact with the splicing machinery in such a way that splicing produces a truncated RNA messenger of one or more exons but whose overall reading frame is not modified, which makes it possible to obtain a truncated but partially functional protein (Van et al., 2008).

"Aptamer" refers to a modified oligonucleotide selected from a random bank of sequences according to its affinity for a biological ligand intended for its therapeutic use. Aptamers differentiate from other nucleic acid sequences by their capacity to fold into a tertiary structure to create a binding pocket making it possible to interact precisely and specifically with the target. Aptamers have numerous therapeutic applications (Kaur and Roy, 2008).

"Nucleic acid for the modification of alternative splicing" refers to a nucleic acid making it possible to modify pre-messenger RNA with an aim of obtaining the expression of a modified protein.

Preferably, the nucleic acid able to modulate a protein function is selected from an antisense oligonucleotide, an oligonucleotide for exon skipping or an oligonucleotide for the modification of alternative splicing or an interfering RNA, even more preferentially an interfering RNA, and/or the modified forms of said nucleic acids, such as the morpholino, phosphorothioate, phosphoroamidate and 2'-O-methyl forms.

In an even more preferred manner, said interfering RNA is a small interfering RNA (siRNA) or a microRNA (miRNA), most preferably a small interfering RNA.

Preferably, the nucleic acid has a size less than 200 nucleotides, more preferably less than 100 nucleotides, in a particularly preferred manner less than 50 nucleotides, and in an even more preferred manner less than 30 nucleotides. Most preferably, the nucleic acid has a size between 20 and 25 nucleotides.

Preferably, when the small nucleic acid is a small interfering RNA, it has a size, comprised between 19 and 25 nucleotides.

Preferably, when the small nucleic acid is a microRNA, it has a size between 20 and 25 nucleotides.

Preferably, when the small nucleic acid is an antisense oligonucleotide, it has a size comprised between 13 and 25 nucleotides.

Preferably, when the small nucleic acid is an oligonucleotide for exon skipping, it has a size comprised between 17 and 31 nucleotides.

Preferably, when the small nucleic acid is an oligonucleotide for the modification of alternative splicing, it has a size comprised between 15 and 30 nucleotides.

Preferably, when the small nucleic acid is an aptamer, it has a size comprised between 20 and 80 nucleotides.

Preferably, the concentration in nucleic acid in the composition according to the present invention for an in vitro use is comprised between 1 nM and 100 nM, even more preferentially between 5 nM and 50 nM, and most preferably between 15 nM and 25 nM.

Preferably, the concentration in nucleic acid in the composition according to the present invention for an in vivo use is between 0.1 mg/kg and 2.5 mg/kg, even more preferentially between 0.3 mg/kg and 1 mg/kg, and most preferably between 0.4 mg/kg and 0.6 mg/kg.

A preferred composition according to the present invention is such that the anionic macromolecule is alginic acid, the cationic lipid is a lipopolyamine, preferably 2-{3-[bis-(3-amino-propyl)-amino]-propylamino}-N-ditetradecyl carbamoyl methyl-acetamide (RPR209120), and the nucleic acid of size less than or equal to 200 nucleotides is a nucleic acid able to modulate a protein function, said nucleic acid is preferably selected from a siRNA or an oligonucleotide for exon skipping or the modification of alternate splicing, said compound RPR209120 being advantageously formulated as a liposome by association with a neutral lipid such as DOPE.

Preferably, the composition according to the invention is such that the anionic macromolecule is alginic acid, the cationic lipid is compound RPR209120 and the nucleic acid of size less than or equal to 200 nucleotides is a small interfering RNA, said compound RPR209120 being advantageously formulated as a liposome by association with a neutral lipid such as DOPE.

Another preferred composition according to the present invention is such that the anionic macromolecule is polyglutamic acid, the cationic lipid is a lipopolyamine, preferably compound RPR209120, and the nucleic acid of size less than or equal to 200 nucleotides is a nucleic acid able to modulate a protein function, said nucleic acid being preferably selected from a siRNA or an oligonucleotide for exon skipping or the modification of alternate splicing, said compound RPR209120 advantageously formulated as a liposome by association with a neutral lipid such as DOPE.

Preferably, the composition according to the present invention is such that the anionic macromolecule is polyglutamic acid, the cationic lipid is compound RPR209120 and the nucleic acid of size less than or equal to 200 nucleotides is a small interfering RNA, said compound RPR209120 being advantageously formulated as a liposome by association with a neutral lipid such as DOPE.

Another preferred composition of the present invention is such that the anionic macromolecule is polyphosphate, the cationic lipid is a lipopolyamine, preferably the compound RPR209120, and the nucleic acid of size less than or equal to 200 nucleotides is a nucleic acid able to modulate a protein function, said nucleic acid being preferably selected from a siRNA or an oligonucleotide for exon skipping or the modification of alternate splicing, and wherein said compound RPR209120 is advantageously formulated as a liposome by association with a neutral lipid such as DOPE.

Preferably, the anionic macromolecule is pre-associated with the nucleic acid. By "Pre-associated anionic macromolecule", one means that the nucleic acid is contacted with the anionic macromolecule prior to the contacting with the cationic lipid, which enables the formation of a nucleic acid/anionic macromolecule mixture. Preferably, the anionic macromolecule/nucleic acid ratio is comprised between 0.5 and 4 (weight/weight), preferably between 1 and 2, more preferably equal to 1.

The mixture thus formed is then contacted with the cationic lipid, which makes it possible to obtain the anionic macromolecule/nucleic acid/cationic lipid complex. Preferably, the contacting of the mixture with the cationic lipid is carried out volume to volume. In the complex thus obtained, said anionic macromolecule, said cationic lipid and said nucleic acid are noncovalently associated.

Thus, advantageously the inventive composition can comprise:
(1) an anionic macromolecule except for nucleic acids,
(2) a cationic lipid, and
(3) a nucleic acid of size less than or equal to 200 nucleotides;
wherein said anionic macromolecule, said cationic lipid and said nucleic acid are noncovalently associated.

Preferably, the composition of the present invention is present in a medium containing cells to be transfected, under conditions such that there is:
passage of the anionic macromolecule/cationic lipid/nucleic acid complex from the medium into the cell cytoplasm,
release of the nucleic acid involved in the aforesaid complex into the cell cytosol and/or the cell nucleus.

As indicated above, the compositions according to the invention can be used for the transfer of nucleic acids into cells in vivo, in vitro or ex vivo. In particular, the compositions according to the invention can be used to transfer in a very effective manner nucleic acids into numerous types of cells, and in particular into certain types of cells that are usually difficult to transfect.

Thus, the present invention relates to a method for transferring a nucleic acid into cells, said method comprising the contacting of said cells with a composition according to the invention. Preferably, said method is an in vitro or ex vivo method.

The cells can be eukaryotic, in particular animal, plant or human cells.

In a particularly advantageous embodiment, the composition of the present invention further comprises a targeting element making it possible to direct the transfer of the nucleic acid, such as an intracellular targeting element (nucleus, etc.) and/or an extracellular targeting element (targeting of certain types of cells/tissues).

Among the targeting elements that can be used in the context of the invention, one can cites sugars, peptides, oligonucleotides, lipids or proteins. Advantageously, they are sugars, peptides or proteins such as antibodies or antibody fragments, cell receptor ligands or fragments of same, receptors or receptor fragments, etc. In particular, they can be ligands of growth factor receptors, cytokine receptors, cell lectin receptors or adhesion protein receptors. One can also cite transferrin receptor, HDL and LDL. The targeting element can also be a sugar, making it possible to target asialoglycoprotein receptors, or an antibody Fab fragment making it possible to target the immunoglobulin FC fragment receptor.

The present invention also relates to a pharmaceutical composition comprising a composition according to the present invention and a pharmaceutically acceptable carrier. Such a pharmaceutical composition can be formulated for administration to mammals, including man. Posology varies according to the treatment and the affection in question. Such a pharmaceutical composition is prepared in order to be able to be administered by the subcutaneous, intramuscular, intravenous, transdermal, intranasal, intraocular, oral, sublingual, local, rectal, intratumoral, intrathecal, intracerebroventricular or intraperitoneal route, or by bladder instillation. Examples of pharmaceutically acceptable carriers include aqueous suspensions, isotonic saline solutions or sterile and injectable solutions that contain pharmacologically compatible dispersion agents and/or wetting agents.

The doses of nucleic acid used and the number of administrations can be adapted as a function of various parameters, notably as a function of the mode of administration used, the pathology concerned, the nucleic acid to be administered or the duration of the treatment sought.

The present invention also relates to the use of a vector composition comprising:
(1) an anionic macromolecule except for nucleic acids, and
(2) a cationic lipid such as defined above,
for the preparation of a composition intended for the intracellular delivery of nucleic acid.

The present invention also relates to the use of a vector composition comprising an anionic macromolecule and a cationic lipid as a pharmaceutically acceptable vector for a nucleic acid of size less than or equal to 200 nucleotides, such as an interfering RNA. The anionic macromolecule, the lipid and the nucleic acid of size less than or equal to 200 nucleotides are as defined above.

The present invention also relates to a composition of the invention for its use as a drug. Preferably, said drug is intended for the treatment of a pathology associated with a dysfunction of a protein function.

In the present invention, "pathology associated with a dysfunction of a protein function" refers to a pathology related to one or more proteins whose function is disrupted (catalysis, transport, communication, signaling, recognition, structure, etc.).

Said pathology can be selected from inflammatory diseases such as polyarthritis, rheumatism, cancer, viral infections such as hepatitis, parasitic or microbial infections, autoimmune diseases such as lupus erythematosus, cardiac or hepatic fibrosis, monogenic diseases related to dominant mutations such as Huntington's chorea, achondroplasia, amyotrophic lateral sclerosis or Lou Gehrig's disease, pathologies related to exon skipping such as Duchenne muscular dystrophy and polymyositis and neurodegenerative diseases such as Alzheimer's disease.

Preferably, the pathology is chosen among polyarthritis, rheumatism, cancer, hepatitis, lupus erythematosus, cardiac or hepatic fibrosis, Huntington's chorea, achondroplasia, amyotrophic lateral sclerosis or Lou Gehrig's disease, Duchenne muscular dystrophy and polymyositis, and Alzheimer's disease. In a particularly preferred manner, the pathology is selected from polyarthritis, hepatitis, lupus erythematosus, cardiac or hepatic fibrosis, Duchenne muscular dystrophy or polymyositis.

These various pathologies could be treated using the small nucleic acids as defined in the present invention present in the composition, said nucleic acids being able to modulate a protein function. For example, the protein functions that can be modulated using the small nucleic acids of the present invention are those related to:

- TNF-alpha, IL-1, IL-6, IL-18, Akt, GG2-1 and ASC for rheumatoid arthritis,
- interferon-alpha and IL-10 for lupus erythematosus,
- TNF-alpha for polymyositis,
- TNF-alpha for Crohn's disease,
- viral genes during a viral infection, such as the core region of the hepatitis B virus,
- EMCV IRES (encephalomyocarditis virus internal ribosome entry site), NS3 and NS5B, (non-structural protein 3 and 5B) and NA (neuraminidase) genes in hepatitis C,
- caspase 8 and Fas genes in acute liver failure (ALF),
- TGF, PDGF and TNF genes in hepatic fibrosis,
- VEGF, VEGFR1 and VEGFR2 genes in age-related macular degeneration (AMD),
- VEGF, VEGFR1 and VEGFR2 genes in diabetic retinopathy,
- VEGF, VEGFR1 and VEGFR2 genes in cancer (antiangiogenic and antivascular strategies),
- the FGFR3 gene in achondroplasia,
- the SOD1 gene in amyotrophic lateral sclerosis,
- the HD gene Huntington's chorea,
- the dystrophin gene in Duchenne muscular dystrophy (by exon skipping),
- the β-secretase (BACE1) gene in Alzheimer's disease.

According to a final aspect, the present invention relates to a method for preparing a composition of the present invention, comprising:

a) a step of contacting the anionic macromolecule as defined above with the nucleic acid as defined above, for the formation of a mixture,
b) a step of contacting the cationic lipid as defined above with the mixture obtained in step a), for the preparation of the composition.

The present invention also relates to a method of treatment of a pathology associated with a dysfunction of a protein function by administration to the subject to be treated of a composition according to the invention.

The invention will be better understood upon consideration of the examples and figures which follow.

FIGURES

EXAMPLES

Example 1

Materials and Methods

Figure 1A:
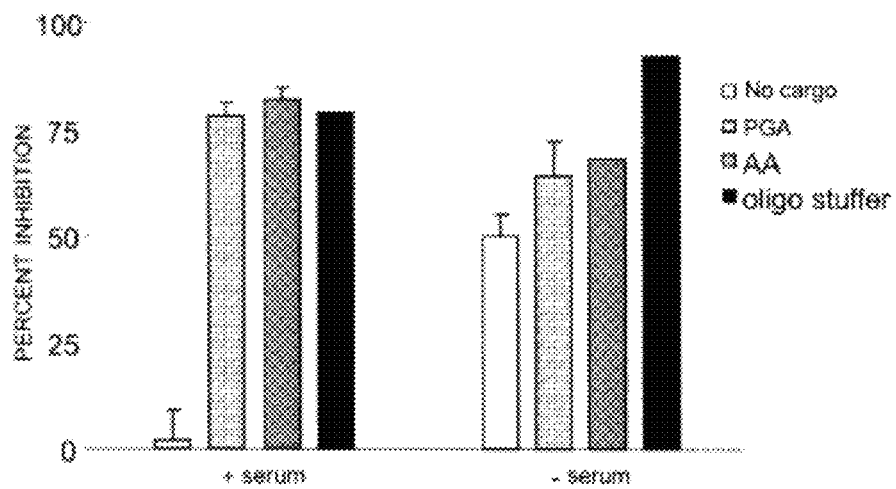
FIGS. 1 (A and B) represent the percentage of inhibition of the expression of luciferase by various formulations of siRNA in the presence or in the absence of an anionic macromolecule.

The compound 2-{3-[bis-(3-amino-propyl)-amino]-propylamino}-N-ditetradecyl carbamoyl methyl-acetamide (RPR209120) is synthesized in the laboratory according to the protocol described in the U.S. Pat. No. 6,171,612.

The compound RPR120535 (2-{3-[3-(3-amino-propylamino)-propylamino]-propylamino}-N,N-dioctadecyl-acetamide) is synthesized in the laboratory according to the protocol described in the article by Byk et al. (1998, J. Med. Chem., 41, 224-235).

RPR209120 and DOSPA (GIBCO BRL) are lipopolyamines, prepared as liposomes with DOPE. DMRIE (GIBCO BRL) is a quaternary ammonium (1,2-dimyristyloxypropyl-3-dimethyl-hydroxy ethyl ammonium bromide), prepared as liposomes with cholesterol (DMRIE-C).

Dioleyl phosphatidyl ethanolamine (DOPE) was purchased from Avanti Polar Lipids.

Preparation of 209120/DOPE Cationic Liposomes

The lipid RPR209120 (2-{3-[bis-(3-amino-propyl)-amino]-propylamino}-N-ditetradecyl carbamoyl methyl-acetamide), synthesized in the laboratory according to the protocol described in the U.S. Pat. No. 6,171,612 and DOPE (dioleyl phosphatidyl ethanolamine) purchased from AVANTI POLAR LIPIDS, are dissolved in chloroform in equimolar quantities in a small flask. The organic solvent is evaporated under vacuum at 20° C. using a Heidolph rotary evaporator in order to form a lipid film at the bottom of the flask. The film is dried for 2 h and then hydrated with water for injection (WFI) for 4 h at 20° C. and then overnight at 4° C. to form large multilamellar vesicles. The suspension is subjected to sonication (115 V, 80 W, 50-60 Hz, LABORATORY SUPPLIES apparatus) until a homogeneous suspension of liposomes with a diameter of 80-100 nm is obtained.

RPR209120DOPE (1:1) liposomes±lipid with 1%, 3% and 5% PEG2000 (weight/weight of total lipid) are also prepared. An adequate quantity of DSPE-PEG2000, purchased from Avanti Polar, is added to the cationic lipid and DOPE before dissolution in chloroform in the flask.

Preparation of Nucleic Acids

Synthetic siRNAs are purchased from QIAGEN. They are hybridized according to the manufacturer's recommendations before use. The siRNAs are in solution in the buffer provided by the manufacturer at a concentration of 100 µM.

Sequences of the sense strand:
Luc 5'CUUACGCUGAGUACUUCGA3' (targeted toward luciferase): SEQ ID NO: 1.
CTLE 5'UUCUCCGAACGUGUCACGU3' (no target): SEQ ID NO: 2.
TNF-alpha 5'GACAACCAACUAGUGGUGCTT3' (targeted toward mouse TNF-alpha): SEQ ID NO: 3.

The synthetic oligonucleotides are purchased from EUROGENTEC. They are supplied in a 100 µM solution. Their sequence is such that they can hybridize to form a large macromolecule by repetition of their units (oligo-1: 5'ATGTACTTAGCTAGT3' (SEQ ID NO: 4), oligo-2: 5'TACATACTAGCTAAG3' (SEQ ID NO: 5)).

Anionic Macromolecules

Poly-L-glutamic acid (sodium salt) or PGA is purchased from SIGMA ALDRICH: (1) PGA-60k, degree of polymerization 371, average molecular weight 56,000, (2) PGA-4-k, degree of polymerization 28, average molecular weight 4,300.

Alginic acid (sodium salt) is purchased from SIGMA ALDRICH.

Dextran sulfate (DS) (sodium salt) is purchased from SIGMA ALDRICH.

Carboxymethyl cellulose (CMC) (sodium salt) is purchased from SIGMA ALDRICH.

The anionic macromolecules are prepared in solution in water at a concentration of 5 mg/ml.

Preparation of Lipoplexes (Nucleic Acid/Cationic Lipid Complexes and Anionic Macromolecule/Nucleic Acid/Cationic Lipid Complexes)

Lipoplexes are prepared by mixing volume to volume a suspension of cationic liposomes or of cationic micelles (at the appropriate concentration in 150 mM NaCl) with a solution of nucleic acids (plasmid DNA, siRNA) also prepared in 150 mM NaCl. The mixture is prepared under strong agitation for 30 minutes at room temperature. When an anionic macromolecule is added to the formulation, it is mixed with the siRNAs in 150 mM NaCl before being mixed volume to volume with the cationic liposomes or the cationic micelles. The lipoplexes prepared with LipofectAMINE or with DMRIE-C are prepared as described above but the 150 mM NaCl is replaced by OptiMEM (INVITROGEN). The charge ratio corresponds to the number of positive charges provided by the lipid or lipids divided by the number of negative charges provided by the siRNA and the anionic macromolecule.

Determination of the Size and the Zeta Potential of the Complexes

The size and the zeta potential of the liposomes and the particles were determined using a Zetasizer 3000 (MALVERN). The liposomes and lipoplexes are prepared in 150 mM NaCl with a final concentration in siRNA (for the lipoplexes) of 700 nM.

Cell Line

A mouse melanoma cell line (B16-F0, ATCC, CRL-6322) was modified to express in a constitutive manner a reporter gene, firefly luciferase (Luc+, Promega), under the control of the SV40 promoter. After electroporation of the cells in the presence of the plasmid carrying the luc+ gene and a geneticin resistance gene, the cells are selected for their resistance to geneticin; then, a clonal cell line is obtained by limiting dilution of the cells that are resistant and that express luciferase. The cells are maintained in culture in DMEM containing GlutaMAX (FISHER BIOBLOCK), 10% fetal calf serum, streptomycin (100 µg/ml) and penicillin (100 U/ml) at 37° C. in the presence of 5% $CO_2$.

Transfection

The day before, the B16-Luc cells are inoculated in 24-well plates at a density of 40,000 cells per well. The day of transfection, the cells are rinsed with DMEM and then incubated in the transfection medium. The transfection medium contains the lipoplexes prepared as indicated above and diluted to $\frac{1}{10}$ in cell culture medium when the transfection is carried out in the presence of serum, or in DMEM when the transfection is carried out in the absence of serum. In the latter case, 10% of the serum is added to the transfection medium 4 h after the start of the transfection. The cells are incubated at 37° C. in the presence of 5% $CO_2$. Twenty-four hours after the start of the transfection, the transfection medium is replaced by fresh culture medium and then the cells are incubated for an additional period of 24 h.

Assays of Luciferase Activity and of Proteins

At the end of the transfection, the cells are rinsed twice in PBS and then lysed with 200 µl of Cell Culture Lysis Reagent (PROMEGA). After recovery of the lysate and centrifugation to eliminate the cellular debris, luciferase activity is measured on the lysate after addition of the substrate (Luciferase Assay Substrate, PROMEGA) and reading of the light emitted using a microplate reader equipped for luminescence (WALLAC VICTOR, PERKIN ELMER). The activity obtained, expressed in cps (counts per second) is standardized by the protein concentration present in the lysate and determined by a BCA test (INTERCHIM).

Example 2

Anionic Macromolecule Evaluation Methods

The cell tests are carried out on a mouse cell line which continuously expresses a "reporter" protein, i.e., a protein whose activity is easy to measure with precision and in a reproducible way. In this case the reporter is luciferase, which emits light that is easily measurable when it is provided with its substrate molecule, luciferin. Cells expressing luciferase are brought together with various preparations containing a siRNA able to specifically inhibit the expression of luciferase associated with a vector. The light emitted by these cells 48 h after the treatment is measured and compared with cells not having undergone any treatment.

Compositions comprising the cationic liposome, the nucleic acid and the anionic macromolecule are prepared at concentrations from 3 nmol to 8 nmol of cationic lipid per µg of nucleic acid and of anionic macromolecule; the final siRNA concentration used is 20 nM. Compositions prepared under the same conditions but containing a control siRNA (without inhibition activity) are tested in parallel for each experiment in order to observe nonspecific activity. In the majority of the cases presented below, these compositions do not result in any inhibition of luciferase activity.

Example 3

Identification of the Anionic Macromolecule

Figure 1B:
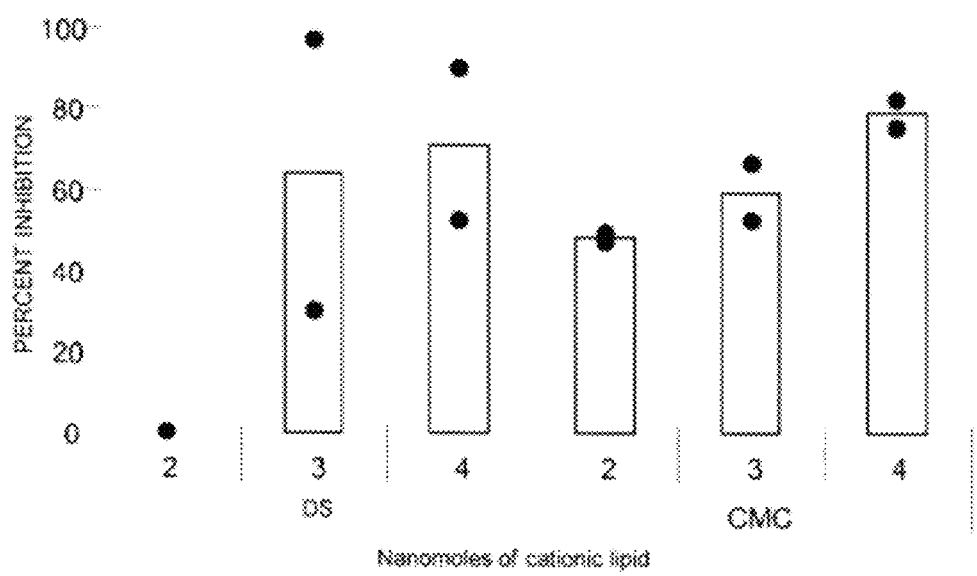

Protocol 0.3 µg of siRNA specific for luciferase is mixed with 0.3 µg of various anionic macromolecules (PGA=polyglutamic acid, AA=alginic acid, DS=dextran sulfate, CMC=carboxymethyl cellulose) and then associated with the cationic liposome RPR209120/DOPE (FIG. 1A: 4 nmol of cationic lipid/µg of mixture (siRNA+anionic macromolecule); FIG. 1B: 2 nmol, 3 nmol, 4 nmol of cationic lipid/µg of mixture (siRNA+anionic macromolecule) before being contacted with the cells for 24 h. Luciferase activity is measured 48 h after the treatment. The results are expressed as a percentage of inhibition relative to cells not having received any treatment (FIG. 1A) or having received control siRNA prepared according to the same formulation (FIG. 1B).

Concerning the results presented in FIG. 1A, the treatment is carried out either in a complete natural cell medium (+ serum) or by temporarily removing the serum, the source of proteins essential for cell growth (− serum). The second condition is often used because it makes it possible to eliminate interference from serum proteins with the preparations but it is quite dissimilar from the conditions in an organism. The first condition is thus closer to the conditions expected in an organism.

Concerning the results presented in FIG. 1B, the treatment is carried out in a complete natural cell medium (+ serum).

Results

The results are presented in FIGS. 1 (A and B).

It should be noted that the formulations with an anionic macromolecule are as effective in the presence of serum as in the absence of serum, whereas the formulation with no anionic macromolecule is effective only in the absence of serum, which justifies the addition of an anionic macromolecule to the formulation to obtain a formulation likely to be effective in the organism. FIGS. 1A and 1B show that all of the anionic polymers tested (namely polyglutamic acid, alginic acid, dextran sulfate and carboxymethyl cellulose) are effective in enabling the inhibition of luciferase. Moreover, in FIG. 1A, it is observed that polyglutamic acid and alginic acid equally enable an increase in gene extinction. This extinction is specific because no extinction is obtained when the siRNA targeted toward luciferase is replaced by a control siRNA having no target.

Example 4

Effect of the Quantity of Anionic Macromolecule Added

Protocol 0.3 µg of siRNA specific for luciferase is mixed with various quantities of polyglutamic acid (PGA), i.e., 0.15 µg, 0.3 µg, 0.6 µg and 1.2 µg of PGA, and then is associated with the cationic liposome RPR209120/DOPE (4 nmol of cationic lipid/µg of mixture of siRNA+anionic macromolecule), before being contacted with the cells for 24 h. Luciferase activity is measured 48 h after the treatment. The results are expressed as a percentage of inhibition relative to cells not having received any treatment.

Results

Figure 2:
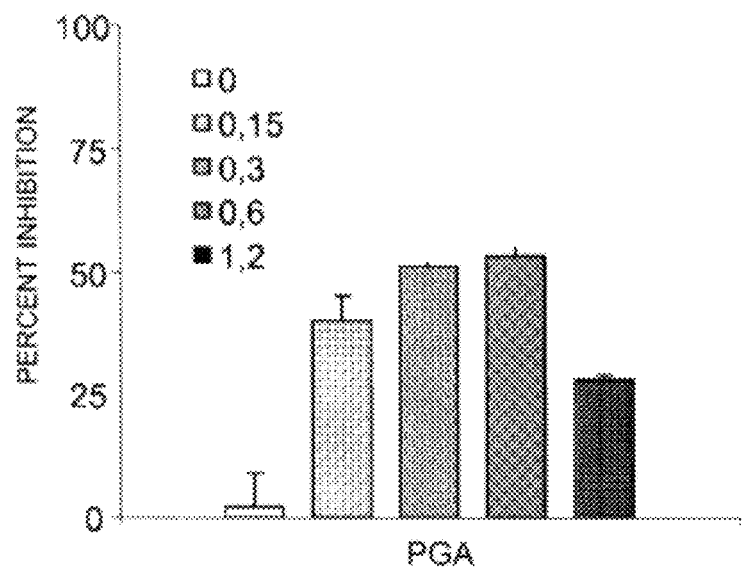
FIG. 2 represents the percentage of inhibition of the expression of luciferase by various formulations of siRNA as a function of the quantity of the anionic macromolecule present.

The results, presented in FIG. 2, show the effect of the quantity of macromolecule added on inhibition. Approximately the same effectiveness is obtained with a siRNA/macromolecule weight/weight ratio of 1/0.5 to 1/2. For a ratio of 1/4, the decrease in inhibition can be explained by the toxicity on the cells of the formulations, which comprise 4 times as many lipids than in the case of the 1/1 ratio.

Example 5

Effect of the Size of the Anionic Macromolecule 0.3 µg of siRNA specific for luciferase is mixed with 0.3 µg of various anionic macromolecules (DNA, PGA-60k (degree of polymerization 371, average molecular weight 56,000), PGA-4-k (degree of polymerization 28, average molecular weight 4,300) and then associated with the cationic liposome RPR209120/DOPE (4 nmol of cationic lipid/µg of mixture of siRNA+anionic macromolecule), before being contacted with the cells for 24 h. Luciferase activity is measured 48 h after the treatment. The results are expressed as a percentage of inhibition relative to cells not having received any treatment.

Results

Figure 3:
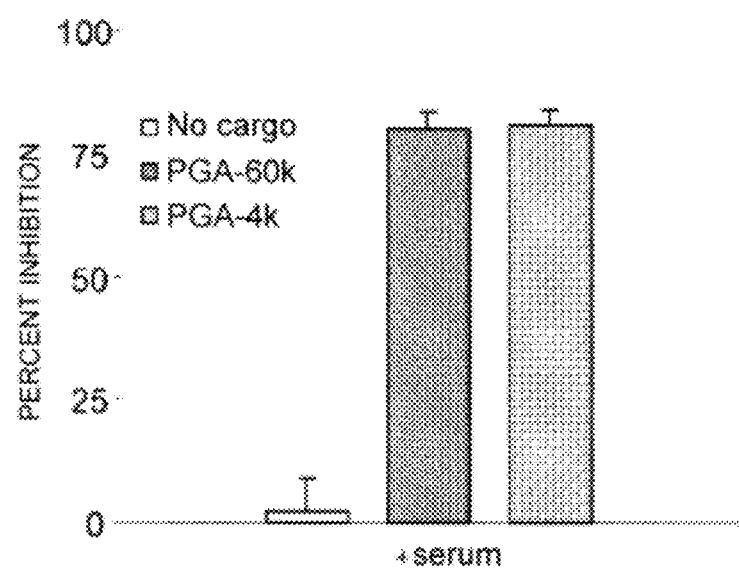
FIG. 3 represents the percentage of inhibition of the expression of luciferase by various formulations of siRNA as a function of the degree of polymerization of the anionic macromolecule.

The results, presented in FIG. 3, show that the percentage of inhibition is independent of the degree of polymerization of the anionic macromolecule.

Example 6

Effect of the Mode of Preparation of the Lipid Vector

Protocol 0.3 µg of siRNA specific for luciferase is mixed with 0.3 µg of various anionic macromolecules (DNA, PGA, AA) and then associated with the cationic lipid RPR120535 prepared as liposomes (by association with a neutral lipid such as DOPE) or as micelles (4 nmol of cationic lipid/µg of mixture of siRNA+anionic macromolecule), before being contacted with the cells for 24 h. Luciferase activity is measured 48 h after the treatment. The results are expressed as a percentage of inhibition relative to cells not having received any treatment.

Results

Figure 4:
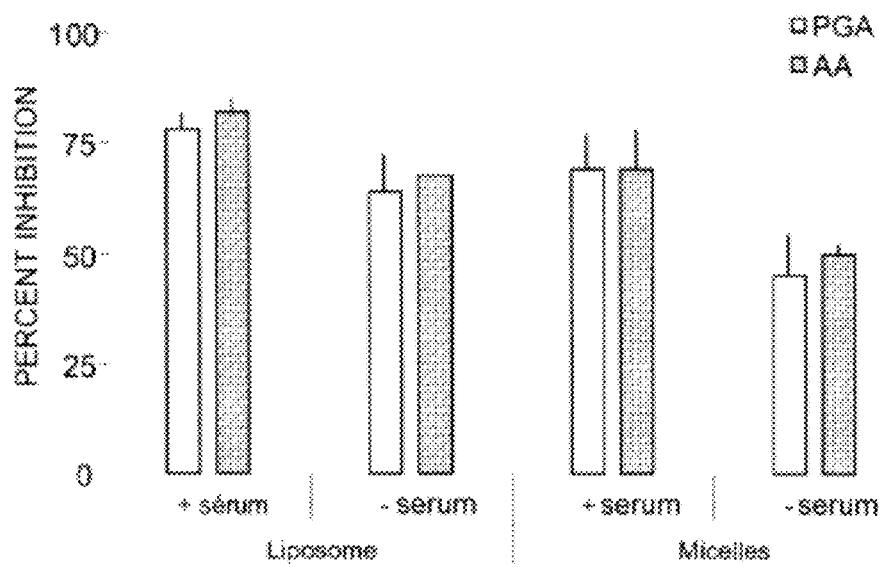
FIG. 4 represents the percentage of inhibition of the expression of luciferase by various formulations of siRNA as a function of the type of vector (micelle/liposome) and of the presence or the absence of serum.

The results, presented in FIG. 4, show that the addition of the anionic macromolecule in the formulation makes it possible to obtain satisfactory effectiveness of luciferase inhibition, whether the cationic lipid is prepared in liposome or micelle form.

Example 7

Effect of the Type of Cationic Lipid

Protocol 0.3 µg of siRNA specific for luciferase is mixed with 0.3 µg of various anionic macromolecules (DNA, PGA, AA) and then associated with various cationic lipids under optimal transfection conditions for each (RPR209120/DOPE, 4 nmol/µg of mixture of siRNA+anionic macromolecule; Lipofectamine and DMRIE-C, 5 µg/µl of mixture (siRNA+anionic macromolecule)) before being contacted with the cells for 24 h. Luciferase activity is measured 48 h after the treatment. The results are expressed as a percentage of inhibition relative to cells not having received any treatment.

Results

Figure 5:
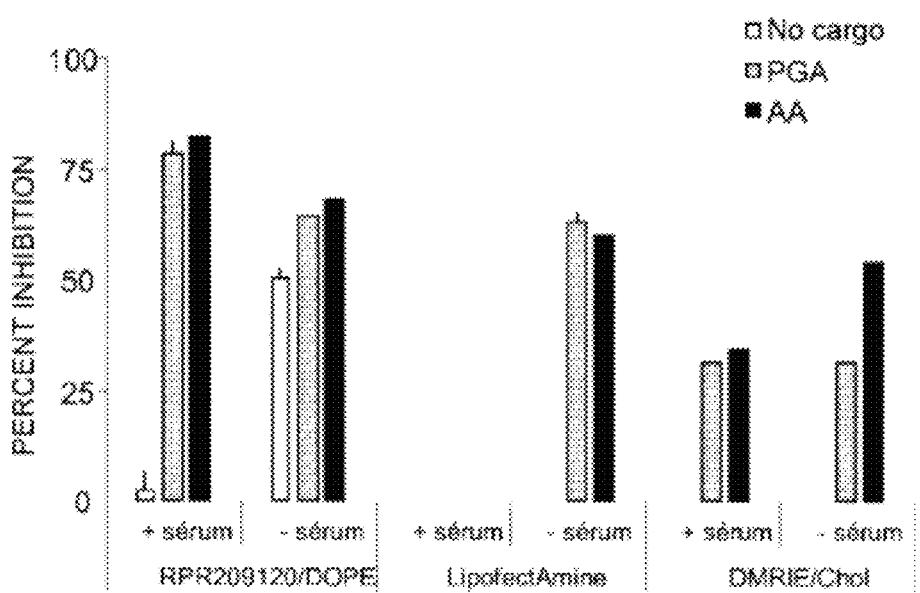
FIG. 5 represents the percentage of inhibition of the expression of luciferase by various formulations of siRNA as a function of the cationic lipid used in presence and in the absence of serum.

The results, presented in FIG. 5, show that the addition of an anionic macromolecule to increase the effectiveness of inhibition of the expression of a gene is applicable to cationic lipids other than RPR209120. Lipofectamine is not effective in the presence of serum, a phenomenon already demonstrated in the literature and well known. DMRIE is less effective than RPR209120.

Example 8

Effect of the Anionic Macromolecule on an Animal Model

Protocol

Five-week-old female Swiss mice are treated by an intraperitoneal injection of lipopolysaccharides (*E. coli* LPS, Sigma Aldrich) in 150 mM NaCl at a dose of 4 mg/kg. A sample of blood from the retro-orbital sinus is drawn 1.5 h later. The TNF-alpha present in the blood is assayed on 100 µl of serum using a DuoSet mouse TNF-alpha assay kit (R&D Systems). Twenty-four hours before treatment by the LPS, the mice receives by intraperitoneal route 5 µg of siRNAs formulated in lipoplexes with the cationic liposome RPR209120/DOPE (6 nmol of cationic lipid/µg of (siRNA+ anionic macromolecule)). It is either formulated alone, or after pre-association with polyglutamic acid (PGA) or alginic acid (AA) before association with the cationic liposome. The results are expressed as a percentage of inhibition relative to mice treated with the same formulation containing a control siRNA.

Results

Figure 6:
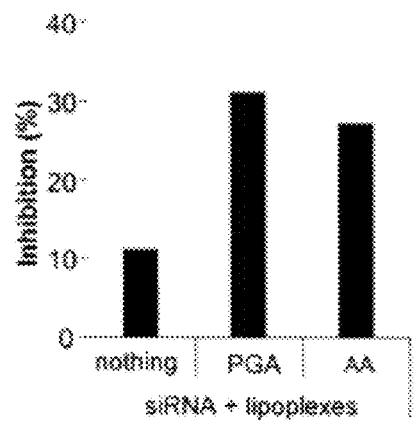
FIG. 6 represents the percentage of inhibition of the level of TNF-alpha in the blood of a mouse.

FIG. 6 shows the percentages of inhibition obtained.

The results show that pretreatment of the mice by siRNA directed against TNF-alpha makes it possible to decrease the level of TNF-alpha in the blood. The decrease observed is improved by the presence of the anionic macromolecule in the formulation.

Example 9

Study of the Complexation of siRNA in the Presence of an Anionic Macromolecule and of Increasing Amounts of Cationic Lipids in the Absence or in the Presence of PEG Protocol RPR209120:DOPE (1:1) liposomes in the presence or in the absence of 1%, 3% and 5% PEG2000 (mole/mole of total lipid) are prepared by sonication.

The lipoplexes formed with increasing concentrations of cationic lipids are prepared (charge ratio from 0.5 to 3) and are analyzed on a polyacrylamide gel in the presence of urea. At the end of the migration, the gels are placed in a bath of SYBR Green to stain the RNA. The results are presented in FIGS. 7 and 8.

Figure 7A:
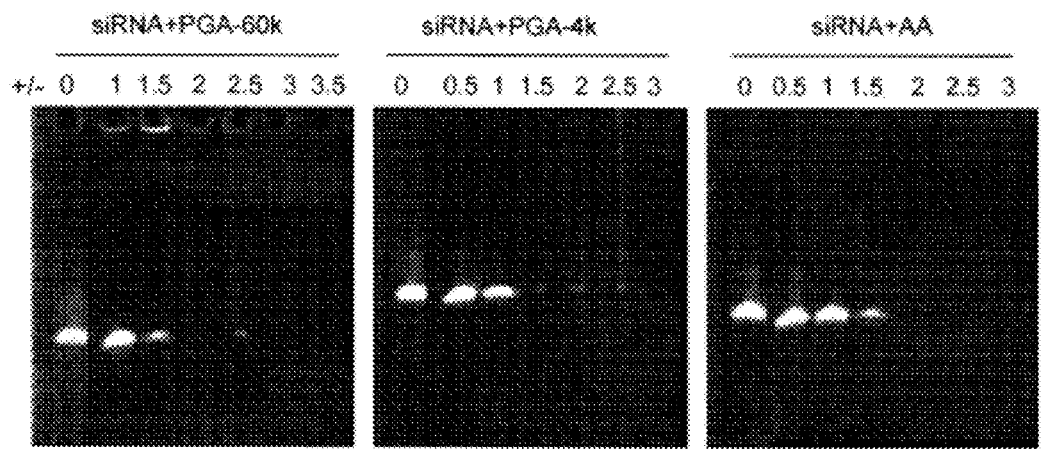
FIGS. 7 (A and B) represents the complexation of siRNA in the presence of an anionic macromolecule and of cationic lipids formed with increasing concentrations in lipids in the absence of PEG (7A) or in the presence of PEG (7B).
Figure 7B:
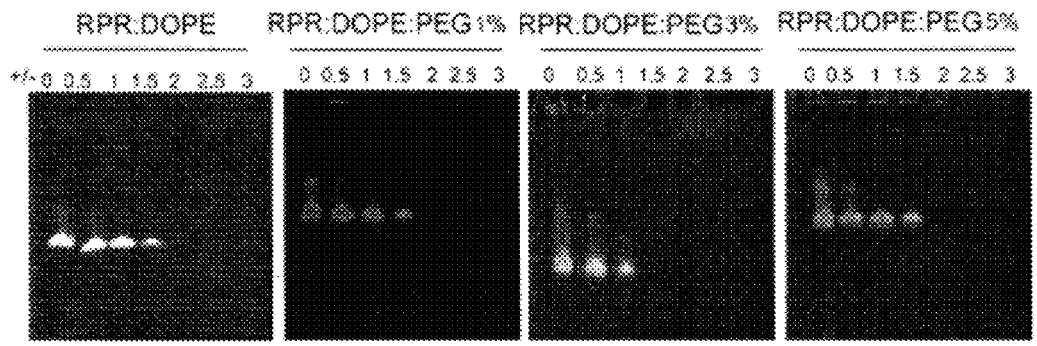

Thus, FIG. 7 shows the complexation profiles of the siRNA by the RPR:DOPE formulations containing the various anionic macromolecules in 150 mM NaCl as a function of the charge ratio. The siRNA/polymer ratio is 1/1 w/w.

FIG. 8 shows the complexation profile of the siRNA by RPR:DOPE: 0%-5% PEG formulations containing alginic acid in 150 mM NaCl as a function of the charge ratio. The siRNA/polymer ratio is 1/1 w/w.

Results

The results presented in FIG. 7 show that the addition of an anionic polymer, whatever its nature, does not modify the capacities of interaction of siRNAs with cationic lipids.

The results presented in FIG. 8 show that the addition of PEG does not modify the capacities of interaction of siRNAs with cationic lipids. The same observation is made regardless of the anionic polymer used. The siRNAs are completely complexed with a charge ratio greater than 2 for all the lipoplexes tested.

Example 10

Figure 8A:
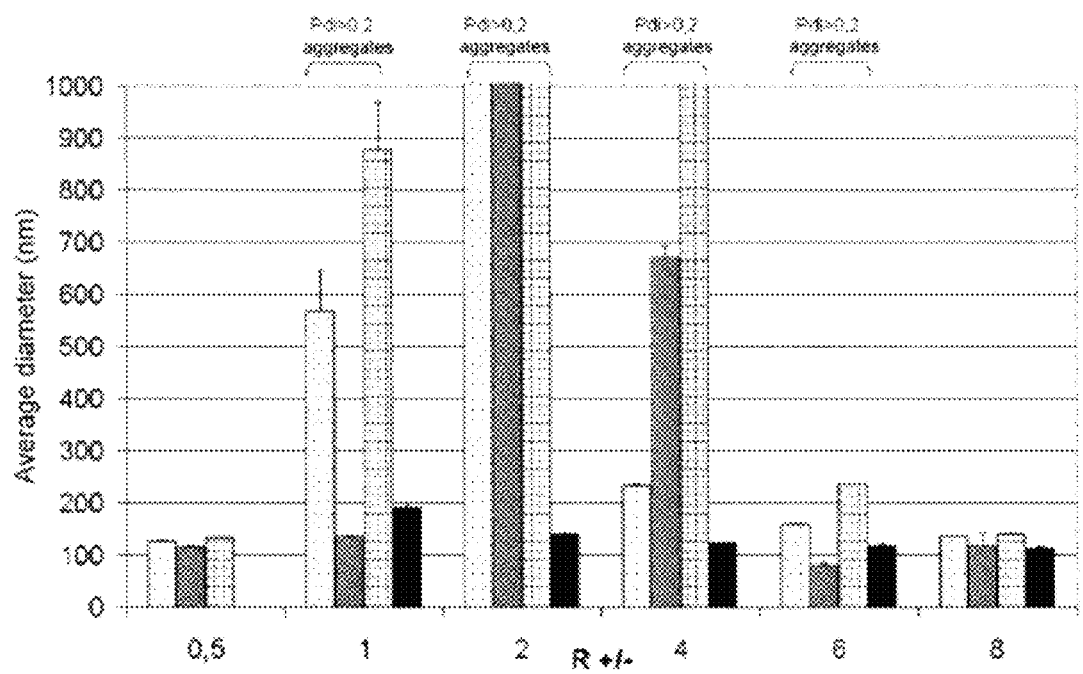
FIGS. 8 (A, B and C) represents the size of the lipoplexes of the invention formed with increasing concentrations in lipids as a function of the quantity and the type of the anionic macromolecule and the percentage of PEG.
Figure 8B:
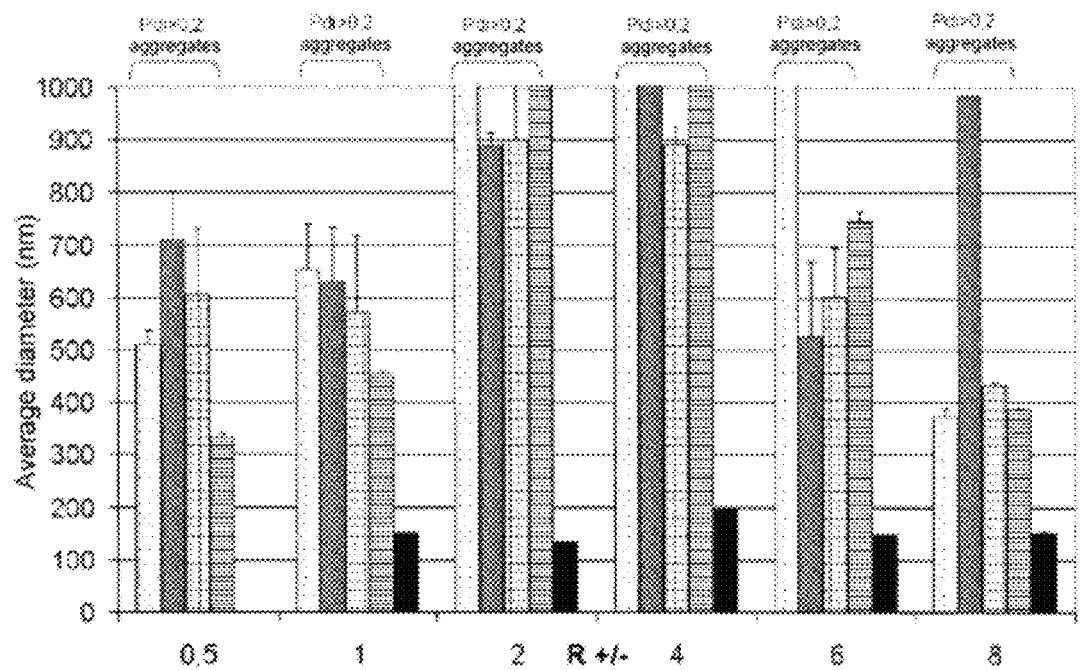
Figure 8C:
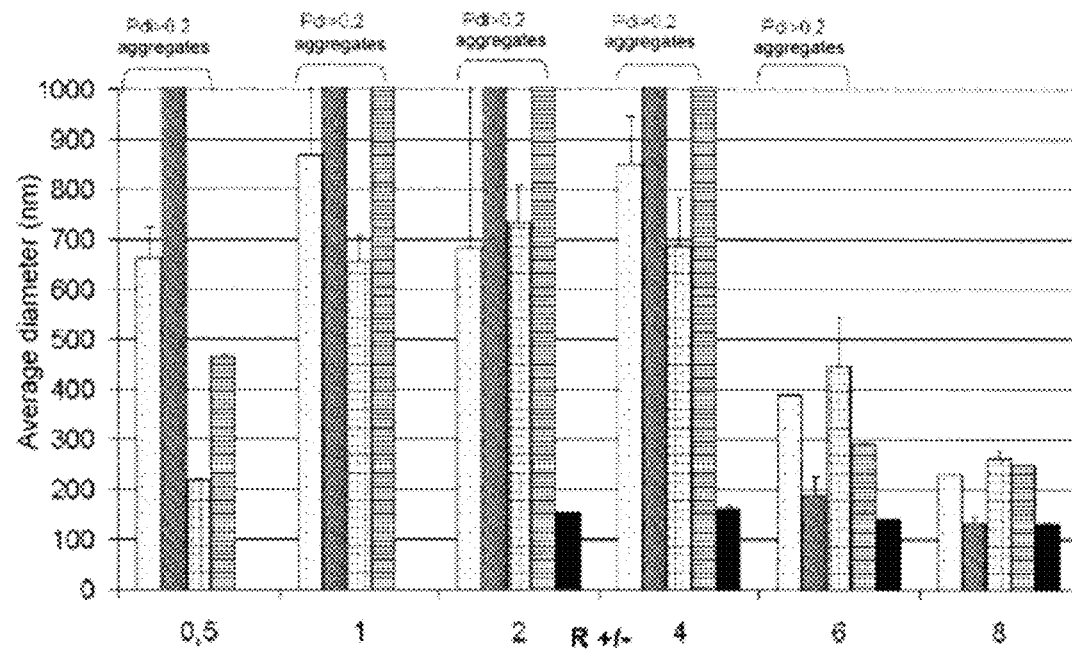

Study of Lipoplex Size as a Function of Increasing Amounts of Cationic Lipids, in the Absence or in the Presence of PEG, as a Function of the siRNA/Anionic Macromolecule Ratio, with Various Anionic Macromolecules Protocol The size of the lipoplexes (siRNA/anionic macromolecule formulated with RPR:DOPE:0%-5% PEG) was measured (by quasi-elastic light scattering in an Malvern Zetasizer apparatus) in 150 mM NaCl as a function of the charge ratio, the quantity of the anionic macromolecule (FIG. 8A: polyglutamic acid (PGA-60k); FIG. 8B: polyglutamic acid (PGA-4-k); FIG. 8C: alginic acid) and the percentage of PEG for each anionic macromolecule. The siRNA/polymer ratio (w/w) was changed from 1/0.5 to 1/2.

Results

FIG. 8 shows that the addition of PEG promotes the formation of smaller particles regardless of the anionic macromolecule used in the inventive lipoplexes. The lipoplexes have a size of approximately 150 nm with 5% PEG, regardless of the charge ratio. The addition of only 1% PEG does not make it possible to sufficiently stabilize the particles; they aggregate in the same manner as with formulations without PEG.

The various anionic macromolecules tested show various colloidal stability profiles. In all cases, a decrease is found in lipoplex size when the charge ratio increases. With higher charge ratios, on the order of 6-8, the lipoplexes are much smaller with polyglutamic acid (PGA-60k) and alginic acid.

Example 11

Study of the Morphology and the Structure of the Lipoplexes in the Absence or in the Presence of PEG with Various Anionic Macromolecules Protocol The morphology of the lipoplexes (siRNA/anionic macromolecules formulated with RPR:DOPE:0% or 5% PEG in 150 mM NaCl) prepared with a charge ratio equal to 6 with various anionic macromolecules was analyzed by transmission electron microscopy (TEM).

Results

Figure 9:
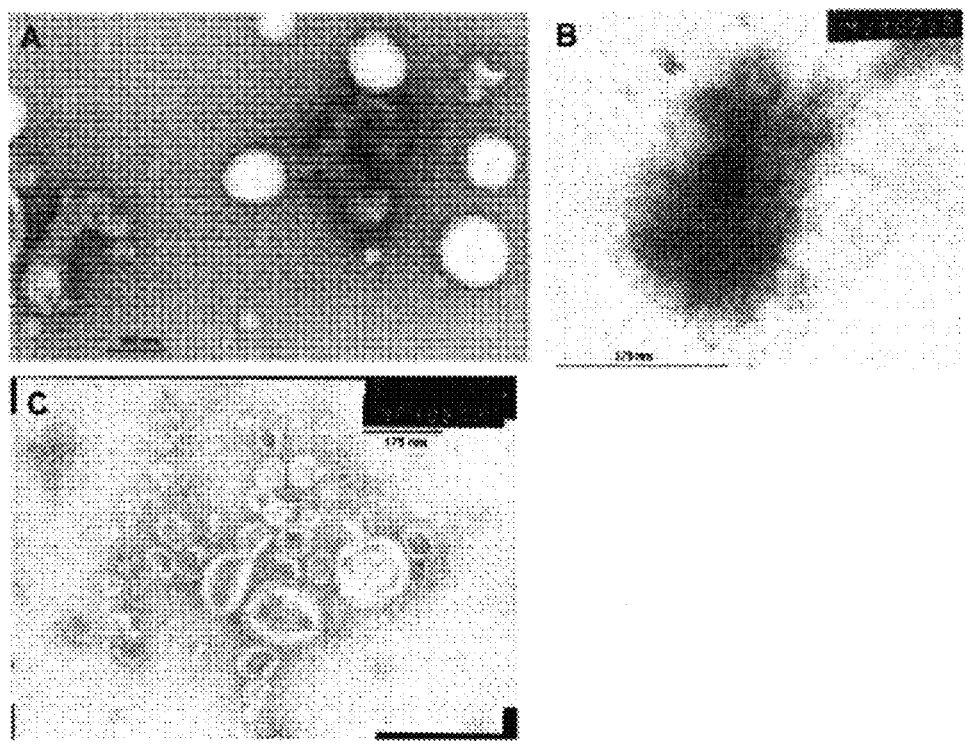
FIGS. 9 (A, B and C) represents the morphology and the structure of the lipoplexes of the invention in the presence or in the absence of PEG.

The images are presented in FIG. 9 (FIG. 9A: alginic acid in the absence of PEG; FIG. 9B: polyglutamic acid (PGA-4-k) in the absence of PEG; FIG. 9C: polyglutamic acid (PGA-4-k) in the presence of 5% PEG).

In absence of PEG, most of the lipoplexes have a layered structure and appear precipitated in large clusters.

In the presence of 5% PEG, most of the lipoplexes have a spherical morphology and appear joined together. The population is heterogeneous, with sizes ranging from 50 nm to 200 nm in diameter on average.

Example 12

Study of the Effectiveness of Transfection of the Lipoplexes in the Absence and in the Presence of PEG with Various Anionic Macromolecules Protocol Transfection studies were carried out on B16 melanoma cells expressing luciferase in a constitutive manner (SV40 promoter). Transfections with various lipoplexes (siRNA/anionic macromolecule formulated with RPR:DOPE in 150 mM NaCl) were carried out for 48 h, while varying the charge ratio, the quantity of anionic macromolecules, the quantity of siRNA and the addition of PEG to the lipoplexes. The experiments are carried out in triplicate, with siRNAs directed against luciferase and nonspecific control siRNA. The results in counts per second (cps) standardized by the concentration in total proteins are expressed relative to transfected cells under the same conditions with control siRNAs. The quantity of total proteins is an indicator of cell proliferation. The transfection experiments were carried out with 20 nM of siRNA.

Results

Figure 10:
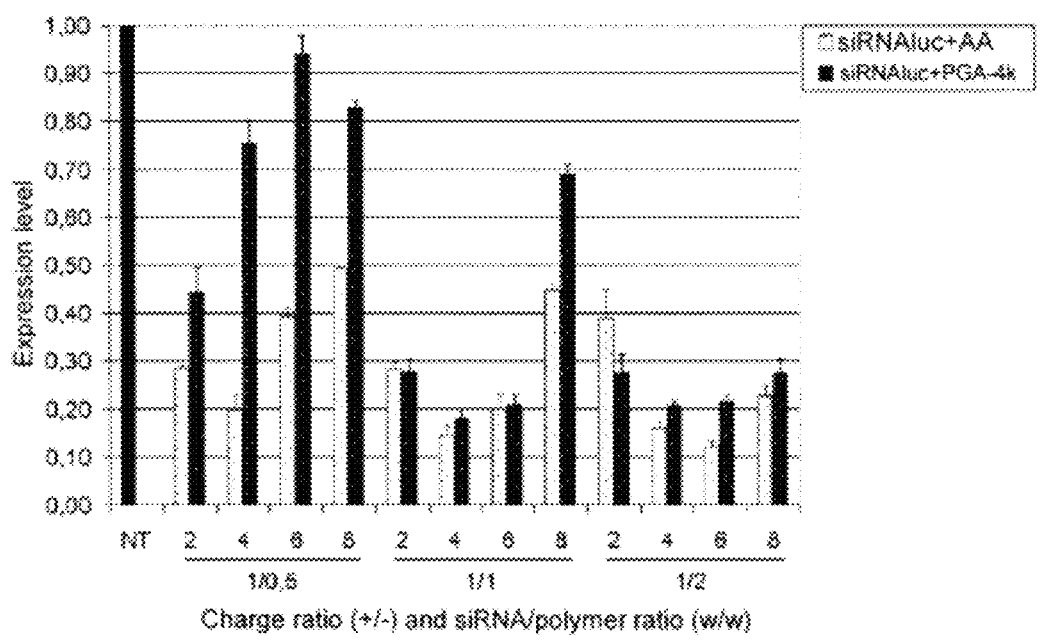
FIG. 10 represents the effectiveness of the inhibition of luciferase by the lipoplexes of the invention as a function of the ratio of charges and of the type and the quantity of the anionic macromolecules.

The results presented in FIG. 10 show that the addition of a larger proportion of anionic macromolecules improves the effectiveness of transfection regardless of the charge ratio.

Transfection experiments were also undertaken with lipoplexes in the presence of PEG. A large decrease in the effectiveness of transfection is then observed when the quantity of PEG increases.

Example 13

Study of the Effectiveness of Transfection of the Inventive Lipoplexes by the Study of the Expression of an Endogenous Gene (Rip or TNFR1)

Protocol

Transfection studies were carried out on B16 melanoma cells expressing luciferase in a constitutive manner (SV40 promoter). Transfections with various lipoplexes were carried out for 48 h, while varying the charge ratio, the quantity of anionic macromolecule and the quantity of siRNA. The experiments are carried out in triplicate, with siRNAs directed against an endogenous gene (RIP (TNF receptor-interacting serine-threonine kinase 1) or TNFR1 (tumor necrosis factor receptor 1)) and nonspecific siRNA controls. After 48 h, the cells are collected and the total RNA is extracted with phenol/chloroform and then reverse-transcribed into cDNA using random primers. The cDNA is then analyzed by quantitative PCR using primers directed against the gene of interest. The accumulation of PCR products is followed by the fluorescence of SYBR Green.

Figure 11A:
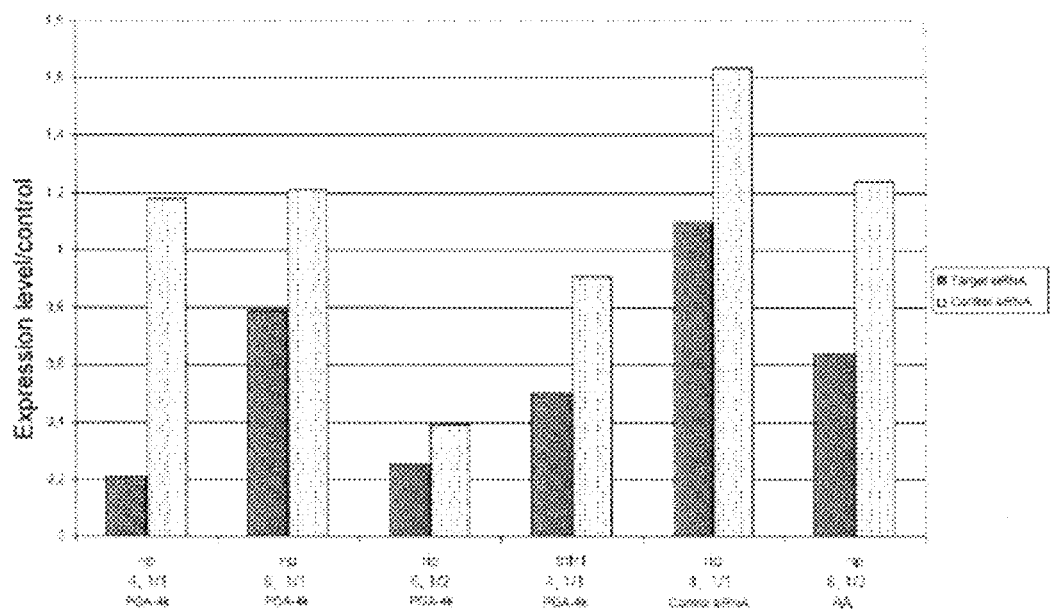
FIGS. 11 (A and B) represents the effectiveness of the transfection of the lipoplexes of the invention by the study of the expression of an endogenous gene (RIP or TNFR1).
Figure 11B:
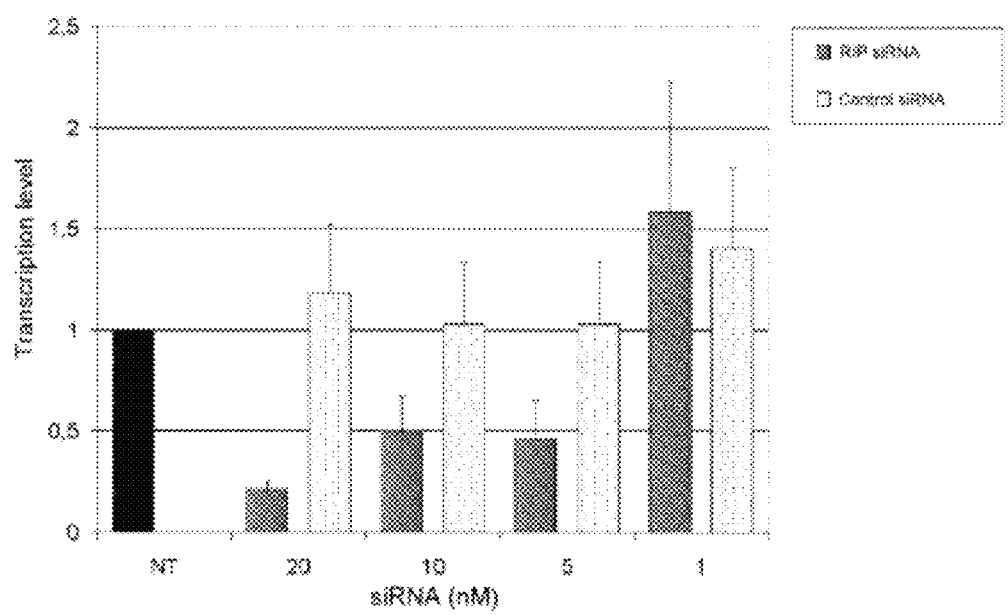

FIG. 11A presents the effectiveness of inhibition of RIP or TNFR1 by the lipoplexes (siRNA/anionic macromolecule formulated with RPR:DOPE in 150 mM NaCl) as a function of the charge ratio, the quantity of anionic macromolecule and the type of anionic macromolecule (polyglutamic acid (PGA-4-k) or alginic acid). The transfections are carried out with 20 nM siRNA. FIG. 11B presents the effectiveness of inhibition of RIP by the siRNA/PGA-4-k lipoplexes formulated with RPR:DOPE in 150 mM NaCl with a charge ratio of 4, 1/1 w/w by decreasing the quantity of siRNA and by replacing it with the anionic macromolecule. The level of non-transfected cells is arbitrarily set at 1.

Results

The results presented in FIG. 11A show an inhibition of 80% of the RIP gene relative to the non-transfected cells. The same experiment carried out on the TNFR1 gene shows only an inhibition of 50%, thus demonstrating that the effectiveness obtained varies according to the siRNA and the gene selected. The addition of an anionic macromolecule to a siRNA before formulation into lipoplexes with a cationic lipid, whether alginic acid or polyglutamic acid (PGA-4-k), enables better effectiveness relative to the formulations without anionic macromolecules (with the addition of control siRNA to maintain the same quantity of lipid).

The results presented in FIG. 11B were carried out by decreasing the quantity of siRNAs and by replacing the siRNAs removed by the anionic macromolecule, thus always maintaining the same concentration in lipoplexes. In this manner a satisfactory effectiveness of transfection is maintained, even with siRNA concentrations ranging from 20 nM to 5 nM.

Example 14

Study of the Stability of the Inventive Lipoplexes in the Presence or in the Absence of PEG in Serum at 37° C.

Protocol

The physical stability of the lipoplexes in serum was evaluated by electrophoresis using a 6% polyacrylamide-urea gel and detection of the siRNAs in SYBR Green II. The lipoplexes are incubated in 50% fetal calf serum and the sample is then dissociated by 1% Triton X-100 which will solubilize the lipids, release the siRNAs and will thus make it possible to quantify them. The stability of the lipoplexes in 50% serum at 37° C. is measured at the following times: 0 h, 2 h, 6 h and 23 h. The results are presented in FIG. 12.

Figure 12:
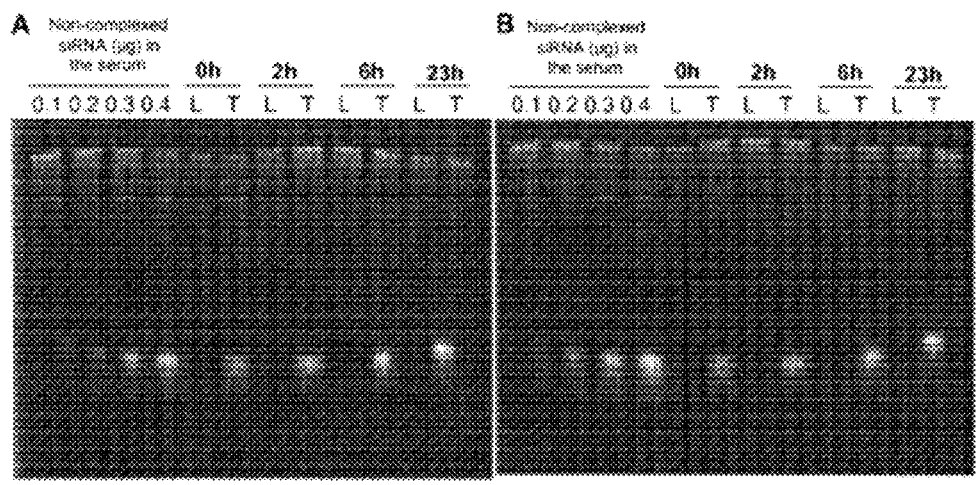
FIGS. 12 (A and B) represents the physical stability of the lipoplexes of the invention in the presence or in the absence of PEG.

FIG. 12 thus presents the stability of the siRNA/PGA1818 lipoplexes formulated with RPR:DOPE:0% or 5% PEG in 150 mM NaCl with a charge ratio of 6, in 50% serum at 37° C. in the absence of PEG (FIG. 12A), or in the presence of 5% PEG (FIG. 12B). In FIG. 12, "L" corresponds to the lipoplexes and "T" to the lipoplexes dissociated by Triton.

Results

The results presented in FIG. 12 show that there is no siRNA free in solution before dissociation with Triton. Two hypotheses can be envisaged: either the lipoplexes are physically stable in the serum and thus are not dissociated, or they dissociate but the siRNA released are degraded by serum nucleases. Dissociation by Triton makes it possible to quantify the siRNA that remain compacted by the lipids.

It can be considered that the lipoplexes with or without PEG with polyglutamic acid are stable for 23 h in 50% serum. The lipoplexes with or without PEG with alginic acid were examined only until 6 h of incubation. They were similarly stable.

Moreover, the addition of an anionic macromolecule such as alginic acid or polyglutamic acid does not involve destabilization of the lipoplexes in the serum.

Example 15

Study of the Cytotoxicity of the Inventive Lipoplexes

Protocol

The cytotoxicity of the inventive lipoplexes is studied with the MTT assay (tetrazolium salt). The tetrazolium ring which it contains is reduced into formazan by the mitochondrial succinate dehydrogenase of active living cells. The color of the medium thus changes from yellow to purplishblue and the result is read by means of a spectrophotometer at 562 nm. The intensity of this staining is proportional to the number of living cells present during the test but also to their metabolic activity. The results are presented in FIG. 13.

Figure 13:
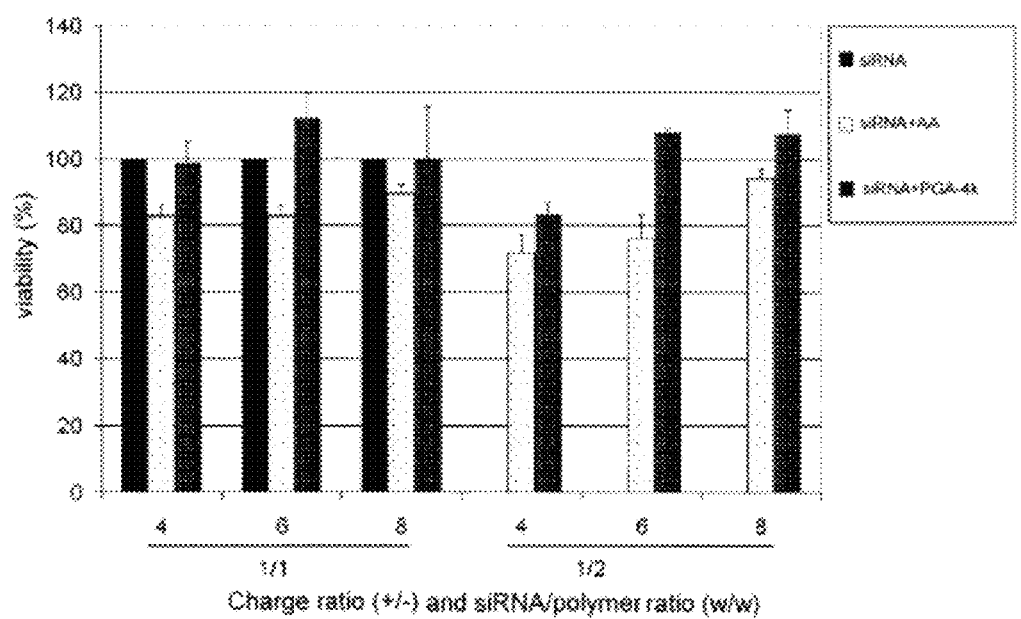
FIG. 13 represents the cytotoxicity of the lipoplexes of the invention.

Thus, FIG. 13 represents the viability of cells transfected by siRNA/anionic macromolecule particles formulated with RPR:DOPE in 150 mM NaCl as a function of the charge ratio and the quantity of the anionic macromolecules. The percentage of viability is expressed relative to the non-transfected cells. The quantity of siRNA is 20 nM. The quantity of total proteins determined by BCA assay is also represented.

The toxicity of the lipoplexes was observed after 48 h with alginic acid or polyglutamic acid (PGA-4-k) with a charge ratio of 4, 6 or 8, and with a siRNA/polymer ratio of 1/1 or 1/2 w/w. The percentages of viability obtained were compared with those obtained for cells transfected with siRNA/RPR:DOPE (the anionic macromolecule was replaced by siRNA to maintain the same quantity of lipid) and for cells cultured with DMSO (positive control of toxicity).

Results

The results presented in FIG. 13 show that overall the addition of anionic macromolecules to a siRNA before formulation into lipoplexes with a cationic lipid results in no additional toxicity, or only very slight toxicity with alginic acid. Toxicity decreases when the charge ratio increases.

Example 16

Study of the Biodistribution of the Inventive Lipoplexes

Protocol

The in vivo model used is a model of metastases of B16 melanoma in the lungs of C57/BL6 mice.

The protocol used is as follows:
At t=0, intravenous injection of $2 \times 10^5$ B16-F0 cells in 20 mice.
At t=15d, three groups are obtained:
group A: 10 mice without tumors (organs harvested at 2 h)
group B: 10 mice with B16 tumors (organs harvested at 2 h)
group C: 10 mice with B16 tumors (organs harvested at 24 h)
For each group:
an intravenous injection (200 µl) is given to 4 mice with 10 µg of control siRNA formulated with a charge ratio of 8 with RPR:DOPE:PE-rhodamine (called "lipo fluo"), and
an intravenous injection (200 µl) is given to 4 mice with 10 µg of siRNA-rhodamine formulated with a charge ratio of 8 with RPR:DOPE (called "sirna fluo")
the two remaining mice are used as controls.

The mice are sacrificed 2 h or 24 h after the injection of the lipoplexes and the organs are observed with a Leica MacroFluo (binocular magnifier equipped with fluorescence illumination), then:
the organs of the mice having received fluo liposomes are preserved at −20° C.,
the organs of the mice having received fluo siRNA are preserved in RNAlater® at 4° C.

For each of the two groups, the organs of the mice having received lipoplexes with lipid-rhodamine are ground in PBS (5 ml per gram of organ), the lipids are extracted in 30 volumes of chloroform:methanol (1:1, v/v) and the fluorescence is assayed in a Wallac Victor apparatus against a range (microplate reader equipped for fluorescence assay). The results, calculated in percentage in the organ of the dose injected, are presented in FIG. 14A.

Figure 14A:
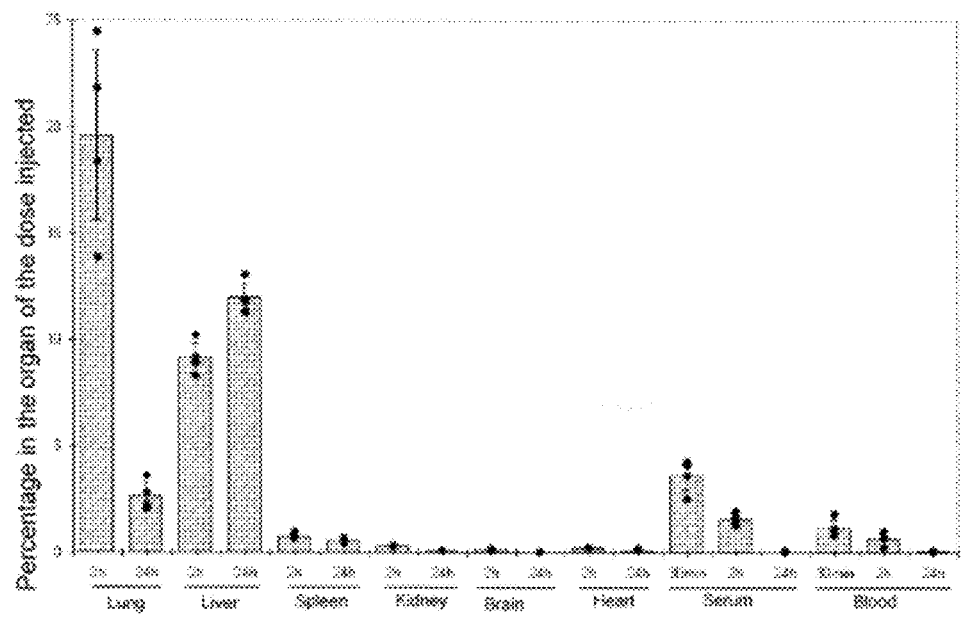
FIGS. 14 (A, B and C) represents the biodistribution in vivo of the lipoplexes of the invention.

Thus, FIG. 14A represents the biodistribution at 2 h and 24 h of the siRNA-polyglutamic acid lipoplexes formulated with RPR:DOPE:rhodamine in 5% glucose with a charge ratio of 8, and then injected intravenously. The mice exhibit metastatic B16 tumors in the lungs.

The siRNAs contained in the organs of the mice having received lipoplexes with siRNA-rhodamine are extracted according to the protocol established with the miRNeasy kit (Qiagen) and fluorescence is assayed with a Wallac Victor apparatus against a range. The results, calculated in percentage in the organ of the dose injected, are presented in FIG. 14B.

Figure 14B:
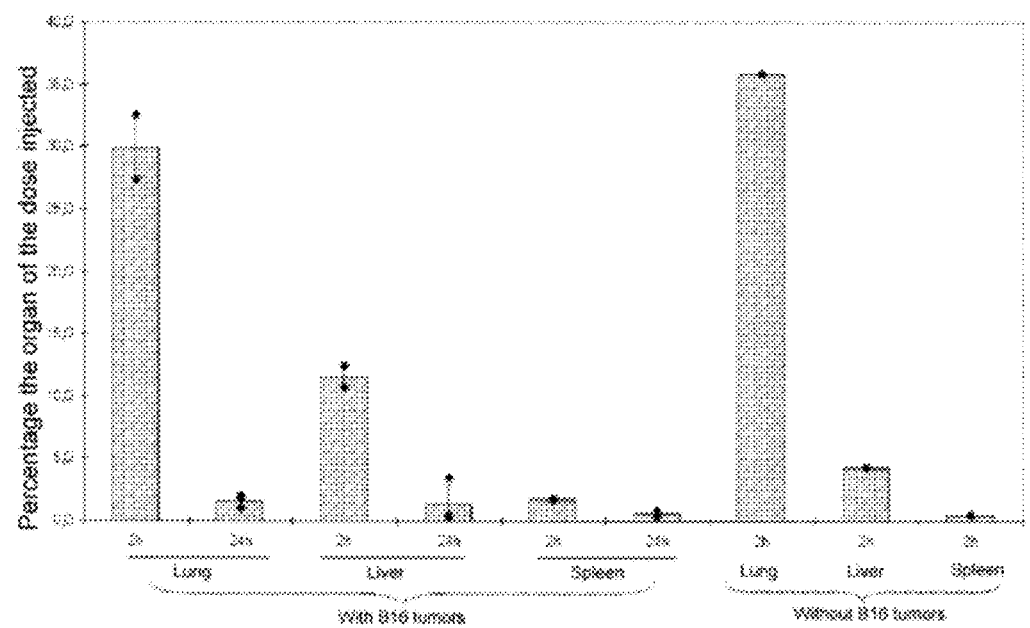

Thus, FIG. 14B presents the biodistribution at 2 h and 24 h of the siRNA-rhodamine lipoplexes with polyglutamic acid formulated with RPR:DOPE in 5% glucose with a charge ratio of 8, and then injected intravenously. The mice exhibited or did not exhibit metastatic B16 tumors in the lungs.

Figure 14C:
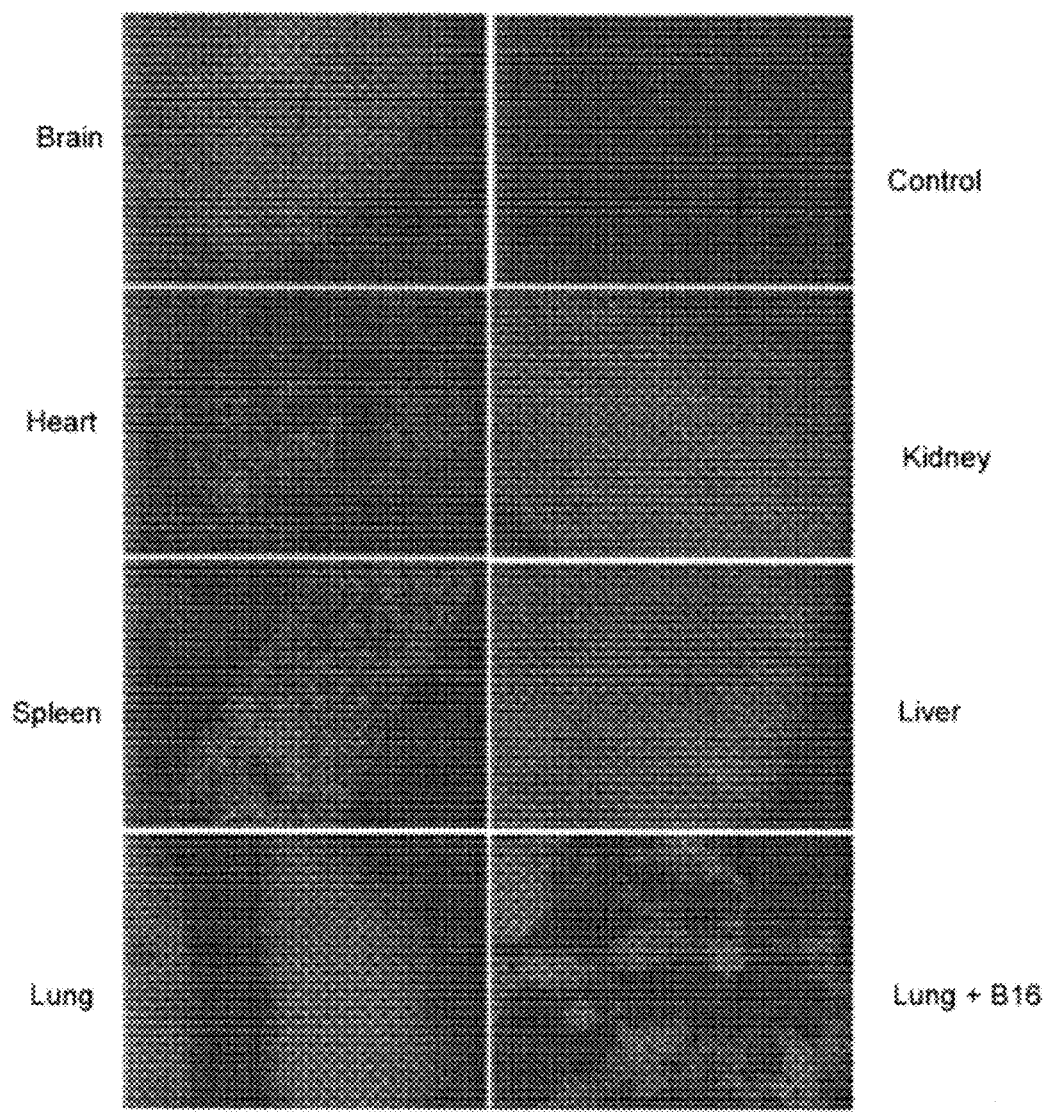

FIG. 14C represents the biodistribution at 2 h of the siRNA polyglutamic acid lipoplexes formulated with RPR:DOPE:rhodamine in 5% glucose with a charge ratio of 8, and then injected intravenously. The mice exhibited or did not exhibit metastatic B16 tumors in the lungs. The controls are identical for all the organs and are thus represented only once. The scales are not identical for the various organs.

Results

As presented in FIGS. 14A and 14B, a distribution is observed principally in the lungs at 2 h (20% of the dose injected for the lipids and the siRNA), which very greatly decreases after 24 h. The liver accumulates approximately 10% of the lipids injected like the siRNAs.

The distribution in the spleen is rather limited, approximately 1%-2% of the dose injected for the lipids and the siRNAs. The other organs, brain, kidney and heart, contain only a negligible quantity of lipid-rhodamine, probably contained in the blood vessels.

The assay of lipid-rhodamine in the blood and the serum show that the lipoplexes are principally free in the serum and little associated with blood cells.

In FIG. 14A, since the scales are different from one organ to the next, the intensity of the fluorescence between the organs should not be compared. For a given organ, the transfected organ and the control organ were observed using the same scale and the controls did not exhibit fluorescence.

As presented in FIG. 14C, the fluorescence observed in the brain highlights the blood vessels, as the lipoplexes probably do not cross the blood-brain barrier. The fluorescence in the heart and in the spleen is rather weak and is concentrated at certain points. Only the fluorescence observed in the kidneys, the lungs and the liver is homogeneous throughout the organ.

CONCLUSION

The addition of an anionic macromolecule to a siRNA before formulation into lipoplexes with a cationic lipid makes it possible to significantly improve the effectiveness of inhibition of a gene, both on cells in culture an also in an animal, without resulting in additional toxicity.

REFERENCES

PATNAIK et al., *PEI-alginate nanocomposites as efficient in vitro gene transfection agents*; Journal of Control Release, 2006, 114(3):398-409

KhoUry et al., *Efficient new cationic liposome formulation for systemic delivery of small interfering RNA silencing tumor necrosis factor alpha in experimental arthritis*. Arthritis Rheum. 2006 June; 54(6): 1867-77.

WU et al., *Let me count the ways: mechanisms of gene regulation by miRNAs and siRNAs*. Mol. Cell. 2008 Jan. 18; 29(1): 1-7. Review.

VAN OMMEN et al., *The therapeutic potential of antisense-mediated exon skipping*. Curr Opin Mol. Ther. 2008 April; 10(2): 140-9. Review.

KAUR and ROY, *Therapeutic applications of aptamers*. Expert Opin Investig Drugs. 2008 January; 17(1): 43-60. Review.

International application WO97/18185 as published May 22, 1997 (Rhone-Poulenc Rorer).

U.S. Pat. No. 6,171,612 delivered on Jan. 9, 2001 (Aventis Pharma).

---

The invention claimed is:

1. A composition comprising:
   (1) an anionic macromolecule other than nucleic acids, wherein the anionic macromolecule is selected from the group consisting of anionic polysaccharides, polyglutamic acid, polyaspartic acid, and salts thereof,
   (2) a cationic lipid selected from the group consisting of 2-{3-[bis-(3-amino-propyl)-amino]-propylamino}-N-ditetradecyl carbamoyl methyl-acetamide (RPR209120) and 1,2-dimyristoyloxypropyl-3-dimethyl-hydroxy ethyl ammonium bromide (DMRIE), and
   (3) a nucleic acid of size less than or equal to 100 nucleotides,
   wherein said anionic macromolecule, said cationic lipid and said nucleic acid (3) are noncovalently associated as a ternary complex, wherein said anionic macromolecule is pre-associated with said nucleic acid before contacting the mixture with the cationic lipid.

2. Composition according to claim 1, wherein the anionic macromolecule has an average molecular weight of between 1,000 Da and 1,000,000 Da.

3. Composition according to claim 1, wherein the cationic lipid is formulated either in the form of micelles, or in the form of liposomes by association with a neutral lipid.

4. Composition according to claim 1, wherein the nucleic acid is able to modulate a protein function, and is selected from the group consisting of antisense oligonucleotide, oligonucleotide for exon skipping or interfering RNA and/or a modified form of same.

5. Composition according to claim 4, wherein the nucleic acid able to modulate a protein function is an interfering RNA.

6. Composition according to claim 1, wherein the anionic macromolecule is polyglutamic acid, the cationic lipid is RPR209120 and the nucleic acid of size less than or equal to 100 nucleotides is a small interfering RNA.

7. Composition according to claim 1, wherein the anionic macromolecule is alginic acid, the cationic lipid is RPR209120 and the nucleic acid of size less than or equal to 100 nucleotides is a small interfering RNA.

8. Pharmaceutical composition comprising a composition as defined in claim 1 and a pharmaceutically acceptable carrier.

9. Composition according to claim 5, wherein the nucleic acid able to modulate a protein function is a microRNA or a small interfering RNA.

10. Composition according to claim 1, wherein the ternary complex is capable of penetrating into a cell.

11. Composition according to claim 1, wherein the anionic macromolecule is polyglutamic acid, alginic acid, heparan sulfate, polyaspartic acid, dextran sulfate, CMBDS, carrageenans, fucans, or salts thereof.

12. Composition according to claim 1, wherein the anionic macromolecule is a sodium salt.

* * * * *

SEQUENCE LISTING

```
<160> NUMBER OF SEQ ID NOS: 5

<210> SEQ ID NO 1
<211> LENGTH: 19
<212> TYPE: RNA
<213> ORGANISM: Artificial
<220> FEATURE:
<223> OTHER INFORMATION: siRNA

<400> SEQUENCE: 1
cuuacgcuga guacuucga                                                    19

<210> SEQ ID NO 2
<211> LENGTH: 19
<212> TYPE: RNA
<213> ORGANISM: Artificial
<220> FEATURE:
<223> OTHER INFORMATION: siRNA

<400> SEQUENCE: 2
uucuccgaac gugucacgu                                                    19

<210> SEQ ID NO 3
<211> LENGTH: 21
<212> TYPE: DNA
<213> ORGANISM: Artificial
<220> FEATURE:
<223> OTHER INFORMATION: siRNA

<400> SEQUENCE: 3
gacaaccaac uagugguget t                                                 21

<210> SEQ ID NO 4
<211> LENGTH: 15
<212> TYPE: DNA
<213> ORGANISM: Artificial
<220> FEATURE:
<223> OTHER INFORMATION: oligonucleotide

<400> SEQUENCE: 4
atgtacttag ctagt                                                        15

<210> SEQ ID NO 5
<211> LENGTH: 15
<212> TYPE: DNA
<213> ORGANISM: Artificial
<220> FEATURE:
<223> OTHER INFORMATION: oligonucleotide

<400> SEQUENCE: 5
tacatactag ctaag                                                        15
```